United States Patent
Kleinberg et al.

(10) Patent No.: US 10,076,481 B2
(45) Date of Patent: Sep. 18, 2018

(54) COMPOSITIONS FOR TREATING PERIODONTITIS AND DENTAL CALCULUS ACCUMULATION

(71) Applicant: The Research Foundation for the State University of New York, Albany, NY (US)

(72) Inventors: Israel Kleinberg, Smithtown, NY (US); Robi Chatterjee, Centereach, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 15/587,265

(22) Filed: May 4, 2017

(65) Prior Publication Data

US 2017/0319452 A1 Nov. 9, 2017

Related U.S. Application Data

(60) Provisional application No. 62/332,201, filed on May 5, 2016.

(51) Int. Cl.
| | |
|---|---|
| *A61K 8/44* | (2006.01) |
| *A61K 8/60* | (2006.01) |
| *A61K 8/55* | (2006.01) |
| *A61K 8/36* | (2006.01) |
| *A61K 8/73* | (2006.01) |
| *A61Q 11/00* | (2006.01) |

(52) U.S. Cl.
CPC ............. *A61K 8/44* (2013.01); *A61K 8/361* (2013.01); *A61K 8/55* (2013.01); *A61K 8/602* (2013.01); *A61K 8/732* (2013.01); *A61Q 11/00* (2013.01); *A61K 2800/87* (2013.01); *A61K 2800/92* (2013.01)

(58) Field of Classification Search
CPC ........................................ A61K 7/16
USPC ........................................ 514/23
See application file for complete search history.

(56) References Cited

U.S. PATENT DOCUMENTS

| | | | | |
|---|---|---|---|---|
| 4,376,762 | A * | 3/1983 | Hauschild | A61K 8/0204 424/401 |
| 5,624,906 | A * | 4/1997 | Vermeer | A61K 8/60 514/23 |
| 6,734,155 | B1 | 5/2004 | Imaj et al. | |
| 8,507,651 | B2 | 8/2013 | Bar-Or | |
| 8,652,495 | B2 | 2/2014 | Porter et al. | |
| 2004/0223921 | A1* | 11/2004 | Rau | A61K 8/19 424/49 |
| 2007/0116800 | A1* | 5/2007 | Prakash | A23G 4/10 426/3 |
| 2012/0020891 | A1 | 1/2012 | Barnes et al. | |
| 2012/0201762 | A1 | 8/2012 | Pilch et al. | |
| 2013/0071439 | A1 | 3/2013 | Losick et al. | |
| 2014/0056951 | A1 | 2/2014 | Losick et al. | |
| 2014/0314691 | A1 | 10/2014 | Eckert et al. | |

FOREIGN PATENT DOCUMENTS

| | | | | |
|---|---|---|---|---|
| JP | 2007-254315 | | 10/2007 | |
| WO | 1996/05803 | | 2/1996 | |
| WO | WO200202060 | * | 1/2002 | ............... A61K 7/00 |
| WO | 2007/076001 | | 7/2007 | |
| WO | 2015/094836 | | 6/2015 | |

OTHER PUBLICATIONS

International Search Report for International Patent Application No. PCT/US2017/019458, dated Apr. 25, 2017 (3 pages).
Biswas, S. D. and Kleinberg, I. 1971. Effect of urea concentration on its utilization, on the pH and the formation of ammonia and carbon dioxide in the human salivary sediment system. Arch. Oral Biol. 16: 759-780.
Denepitiya L. and Kleinberg I. 1982. A comparison of the microbial composition of pooled human dental plaque and salivary sediment. Arch. Oral Biol. 27: 739-745.
Golub, L. M., Borden, S. M., and Kleinberg, I. 1971. Urea content of gingival crevicular fluid and its relation to periodontal disease in humans. J. Periodont. Res. 6: 243-251.
Grases, F., Perelló, J., Sanchis, P., Isern, B., Prieto, R.M., Costa-Bauzá, A., Santiago, C., Ferragut, M.L., and Frontera, G. 2009. Anticalculus effect of a triclosan mouthwash containing phytate: a double-blind, randomized, three-period cross over trial. J. Periodont. Res. 44: 616-621.
Grenby, T.H. 1967. Phytates in decalcification tests in vitro. Arch. Oral Biol. 12: 531-537.
Heaney, R. P., Weaver, C. M., and Fitzsimmons, M. L. 1991. Soybean phytate content: effect on calcium absorption. Am. J. Clin. Nutr. 53: 745-747.
Kaufman, W. and Kleinberg, I. 1971. Effect of pH on calcium binding by phytic acid and its inositol phosphoric acid derivatives and on the solubility of their calcium salts. Arch. Oral Biol. 16: 445-460.
Kleinberg, I. 1967. Effect of urea concentration on human plaque pH levels in situ. Arch. Oral. Biol. 12: 1475-1484.
Kleinberg. I. 1967. Effect of varying sediment and glucose concentrations of the pH and acid production in human salivary sediment mixtures. Arch. Oral. Biol. 12: 1457-1473.
Kleinberg, I. and Hall, G. 1968. pH and depth of gingival crevices in different areas of the mouths of fasting humans. J. Periodont. Res. 3: 109-117.
Kleinberg, I., Craw, D., and Komiyma, K., 1973. Effect of salivary supernatant on the glycolytic activity of the bacteria in salivary sediment. Arch. Oral Biol. 18: 787-798.
Kleinberg, I., Kanapka, J. A., and Craw, D. 1977. The effect of saliva and salivary factors on the metabolism of the mixed oral flora, in Microbial Aspects of Dental Caries. Stiles, H. M., Loesche, W. J. and O'Brien, T. C., Eds. Information Retrieval Inc., Washington, D. C., 433.

(Continued)

*Primary Examiner* — Walter E Webb
(74) *Attorney, Agent, or Firm* — Fish & Richardson P.C.

(57) ABSTRACT

Compositions comprising serine and an organic mono- or multi-phosphate salt and methods of using such compositions to treat and/or prevent periodontal disease and/or dental calculus are provided.

23 Claims, 24 Drawing Sheets

(56) References Cited

OTHER PUBLICATIONS

Kleinberg, I., Kanapka, J. A., Chatterjee, R., Craw, D., D'Angelo, N., and Sandham, H. J. 1979. Metabolism of nitrogen by the oral mixed bacteria, in Saliva and Dental Caries. Kleinberg, I., Ellison, S. A., and Mandel, I. D., Eds. Information Retrieval, Inc., New York, N. Y., 357.
Korayem, M. R., Traudt, M., and Kleinberg, I. 1990. Oxygen uptake and its relation to pH in a human salivary system during fermentation of glucose. Arch. Oral Biol. 35: 759-764.
Jacobson, M. and Kesel, R. G. 1950. Salivary ammonia and its correlation to dental calculus. J. Dent. Res. 29: 364-374.
Takhashi, N. 2005. Microbial ecosystem in the oral cavity: Metabolic diversity in an ecological niche and its relationship with oral diseases. Int. Congr. Ser. 1284: 103-112.
Onosi, M., Tachibana, Y., Nakamura, T., Takakuwa, S., and Ishioka, K. 1957. Preferential sites of the urea hydrolyzing organisms in the mouth. Tokyo Med. Dent. Bull. 4, 253-257.
Salako, N.O. and Kleinberg, I. 1989. Incidence of selected ureolytic bacteria in human dental plaque from sites with differing salivary access. Arch. Oral Biol. 34: 787-791.
Sandham, H. J. and Kleinberg, I. 1973. Effect of fluoride on carbon dioxide and acid formation in salivary sediment mixtures incubated with glucose. Arch. Oral Biol. 18: 211-225.
Singer, D.L. and Kleinberg, I. 1978. Ammonia and urea content of human incisor plaques. Arch Oral Biol. 23: 1983-1987.
Jin, Y. and Yip, H.-K. 2002. Supragingival calculus: Formation and Control. Crit. Rev. Oral Biol. Med. 13: 426-441.
White, Handler, Smith, Principles of Biochemistry, $4^{th}$ Ed., McGraw Hill, p. 597 (1968).
Juerg Solms, "The Taste of Amino Acids, Peptides, and Proteins", J. Agr. Food Chem. vol. 17, No. 4:687-688 (1969).

\* cited by examiner

Pieces of a molar tooth
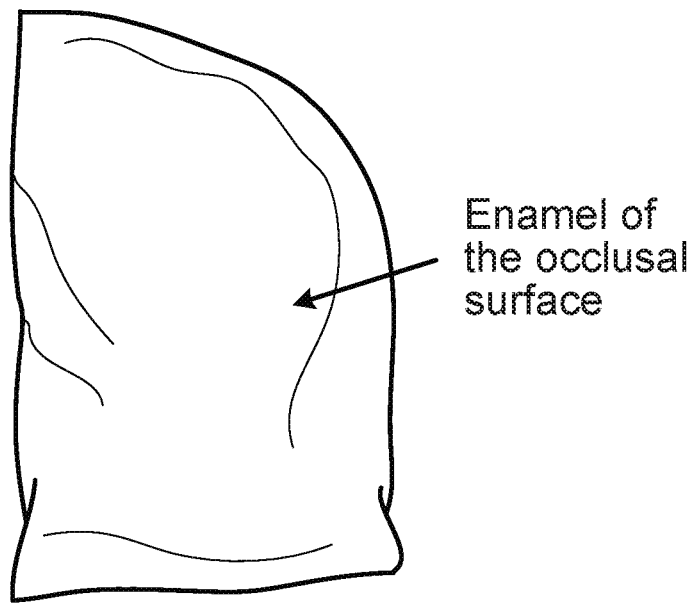
Enamel of the occlusal surface
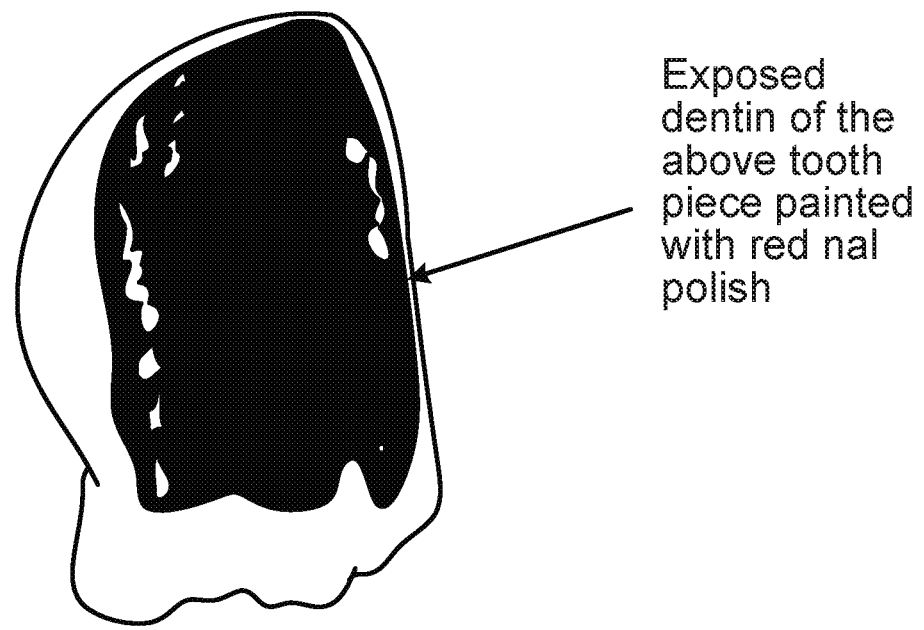
Exposed dentin of the above tooth piece painted with red nal polish
Fig. 23

COMPOSITIONS FOR TREATING PERIODONTITIS AND DENTAL CALCULUS ACCUMULATION

CROSS-REFERENCE TO RELATED APPLICATIONS

This application claims the benefit of U.S. Provisional Application No. 62/332,201 filed May 5, 2016, the contents of which are incorporated herewith.

TECHNICAL FIELD

This disclosure relates to compositions comprising serine and an organic mono- or multi-phosphate salt (e.g., a phytate) for the treatment and/or prevention of periodontitis (e.g., gingivitis) and/or dental calculus formation or development.

BACKGROUND OF THE INVENTION

The human oral cavity contains one of the most densely populated and complex mixed microbial floras that inhabit the human body (Takhashi, N., 2005). One major component of the oral mixed microbial flora is comprised of fermentable carbohydrate metabolizing types of microorganisms that are found particularly in supra-gingival dental sites, namely tooth pits, fissures, and interproximal tooth embrasures. Fermentable dietary carbohydrates and corresponding fermentative oral bacteria are easily and regularly retained in many of these intra-oral locations, sheltered from saliva and readily able to interact to produce abundant acidity and an acidic pH. Such acidity is principally due to the generation of lactic acid, an entity that can readily solubilize tooth calcium phosphate, the dominant mineral element comprising the mineralized tissues (i.e., enamel, dentin, and cementum) of human teeth.

In contrast to acidity, if the environment of the teeth gingivae is alkaline (e.g., because of elevated urea levels that occur in many individuals' gingival crevicular fluid), alkaline conditions may be expected to prevail around the necks of the teeth to where, instead of dental caries, dental calculus and/or periodontitis indices are more evident.

The dental calculus/periodontitis entity involves a mixed microbial flora that mainly populates the regions around the necks of the teeth and extends into adjacent gingival and subgingival dentition sites. The bacteria involved in these locations are mainly non-fermenting. They have been proven to be largely comprised of proteolytic, putrefactive microorganisms that readily metabolize nitrogenous substrates, particularly such derived from the gingivae and adjacent gingival crevicular and periodontal pocket fluids and tissues (Takhashi, N., 2005). Of particular note is that this includes involvement with urea and amino acids, the main end-products of the numerous, common human body amino acids that circulate in the blood vessels throughout the human body. These amino acids and ammonia related thereto are degraded by enzymes in bacteria readily found in gingival crevicular fluid (Golub, L. M., Borden, S. M., and Kleinberg, I., 1971; Onosi, M., Tachibana, Y., Nakamura, T., Takakuwa, S., and Ishioka, K., 1957; Singer, D. L. and Kleinberg, I., 1978).

Upon microbial degradation, gingival and periodontal crevices containing urea are conducive to bacterial degradation to ammonia and can exhibit a high alkaline pH. Such a high pH is an essential element responsible for the easy formation of calcium phosphate deposits (generally referred to as dental plaque or calculus), which readily form around the base of the crowns of teeth (Denepitiya L. and Kleinberg I., 1982; Arch. Oral Biol.; Salako, N. O. and Kleinberg, I., 1989; Jin, Y. and Yip, H.-K., 2002). Left untreated, these crevices promote the proliferation of additional ureolytic and proteolytic bacteria, which in turn promote the formation of additional calculus. Ultimately, this can cause the development of periodontal disease (e.g., gingivitis) (Jacobson, M. and Kesel, R. G., 1950). Central to these processes are the formation and flow of gingival/periodontal crevicular fluid (Golub, L. M., Borden, S. M., and Kleinberg, I., 1971), which characterizes and helps perpetuate these periodontal disease conditions by maintaining a high pH in the environment.

We have previously shown that amino acids can serve as important bacterial substrates and can thereby help facilitate both the accumulation of dental plaque and the development of periodontal disease (including gingivitis, with symptoms including bleeding gums and putrefactive gingivae). For example, urea has been demonstrated to promote tooth and gingival alkalinity, enhancing the accumulation of plaque-causing bacteria on teeth and other surfaces in the oral cavity (Kleinberg, I., 1967, Arch. Oral Biol., 1475-1484). Numerous other amino acids can serve as nitrogenous substrates that contribute to varying degrees of alkalinity and promote periodontal disease, albeit to a lesser degree than urea (Biswas, S. D. and Kleinberg, I., 1971; Golub, L. M., Borden, S. M., and Kleinberg, I., 1971; Kleinberg, I. and Hall, G., 1968). In general, amino acids function to maintain a balance of alkalinity in the oral cavity.

SUMMARY

The present disclosure relates generally to compositions comprising serine and an organic mono- or multi-phosphate salt (e.g., a phytate) which can treat and/or prevent periodontal disease (e.g., gingivitis, e.g., by reducing gingival alkalinity), and/or treat and/or prevent dental calculus accumulation, formation, and/or development.

More specifically, the present disclosure provides an oral composition including serine and one or more organic mono-phosphate or multi-phosphate salts, wherein the pH of the composition is between about 6.0 and about 9.5. The pH of the composition can be, e.g., between about 6.1 and about 6.3. The pH of the composition can be, e.g., between about 6.7 and about 7.0. The organic mono-phosphate or multi-phosphate salts can include, e.g., one or more biological salts. The biological salts can include, e.g., one or more inositol (e.g., phytate) salts. The phytates can include, e.g., sodium phytate. The composition can include, e.g., serine phytate.

Any of the above oral compositions can be provided in an orally acceptable dosage form. The orally acceptable dosage form can be, e.g., a chewable tablet, a piece of chewing gum, a dentifrice, a mouthwash, a rinse, and/or a toothpaste.

Any of the above oral compositions can include one or more devices. One or more surfaces of the device can include, e.g., serine and one or more organic mono-phosphate or multi-phosphate salts, wherein the pH of the surface is between about 6.0 and about 9.5. The pH of the surface can be, e.g., between about 6.1 and about 6.3. The pH of the surface can be, e.g., between about 6.7 and about 7.0. The organic mono-phosphate or multi-phosphate salts can include, e.g., one or more biological salts. The biological salts can include, e.g., one or more inositols (e.g., phytates). The phytates can include, e.g., sodium phytate. The composition can include, e.g., serine phytate. The device can be, e.g., a brush, a piece of floss, a flosser, an irrigator, a mouth guard, a pick, a retainer, a scraper, a spatula, and/or a stick.

The document also provides a method of treating or preventing plaque or periodontal disease (e.g., gingivitis), the method comprising administering an effective amount of any of the above oral compositions to a subject (e.g., a human) having, or at risk of having, plaque or periodontal disease. The oral composition can be, e.g., applied to one or more teeth (e.g., the exposed enamel, dentine, and/or cementum of one or more teeth) of the subject.

The terms "periodontal disease" and "periodontitis" are used interchangeably herein, and refer to one or more periodontal (gum) diseases in an oral cavity (e.g., gingivitis).

The terms "plaque" and "calculus" are used interchangeably herein, and refer to dental plaque or calculus on one or more hard (e.g., teeth) or soft (e.g., mucosal tissue) surfaces in an oral cavity.

As used herein, the term "overnight" is defined as being about 21 hours.

As used herein, the terms "about" and "approximately" are defined as being within plus or minus 10% of a given value or state, preferably within plus or minus 5% of said value or state.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 23 is a series of photographs showing a piece of a molar tooth.

DETAILED DESCRIPTION

Figure 1:
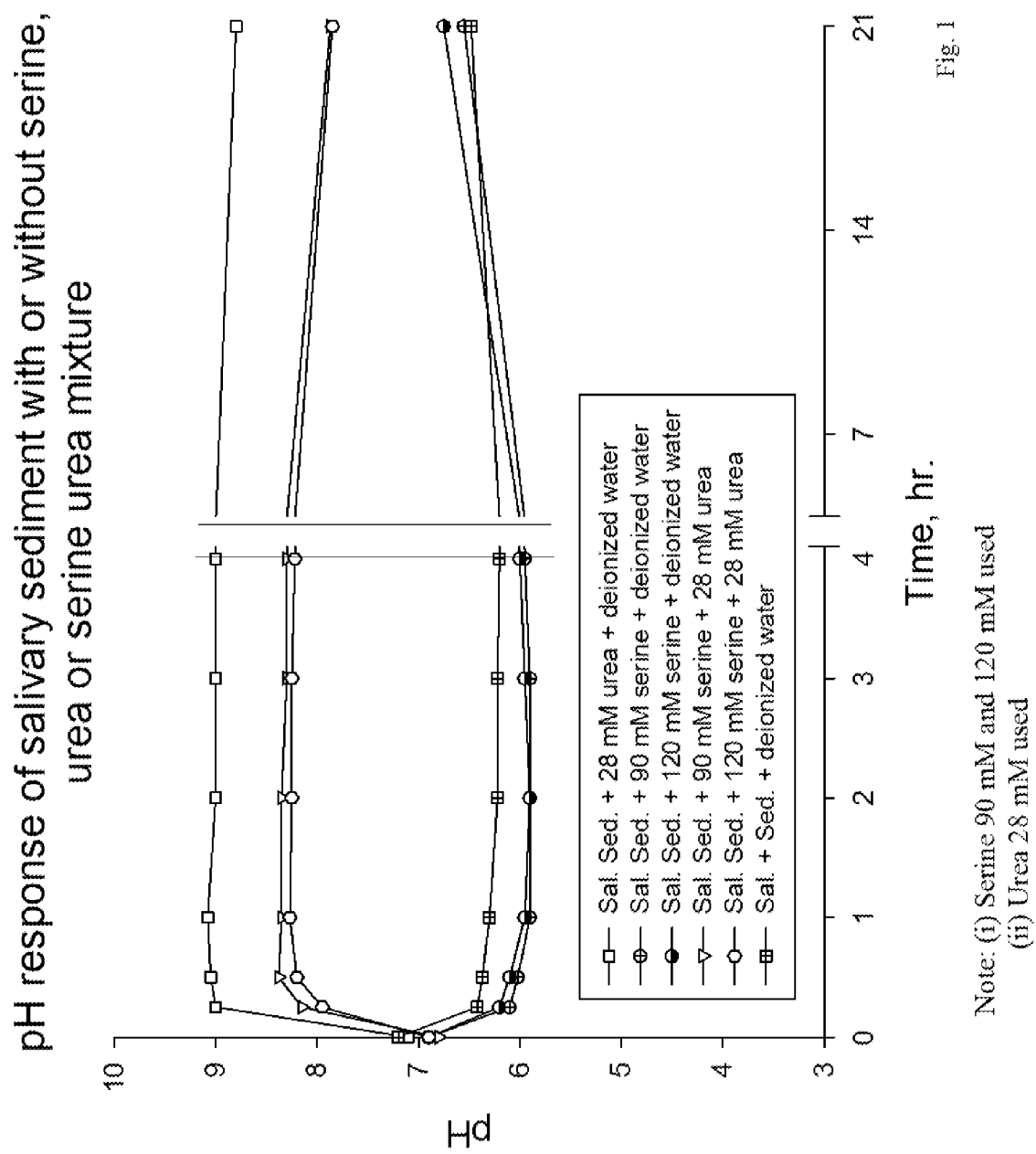
FIG. 1 is a graph showing the pH response of salivary sediment with or without serine, urea, or a mixture of serine and urea.

The present disclosure is based, in part, on the discovery that novel compositions comprising serine and an organic mono- or multi-phosphate salt (e.g., a biological salt such as a phytate) are useful in the treatment and/or prevention of periodontal disease (e.g., gingivitis, e.g., by reducing gingival alkalinity). The compositions disclosed herein are alternately or additionally useful in the treatment and/or prevention of plaque (e.g., by inhibiting, reducing, and/or reversing the accumulation, formation, and/or development of dental calculus).

Multiple aspects of the physiology and pathology of the common amino acids found in the oral cavity and elsewhere in the human body were characterized. In particular, each amino acid was examined to determine whether and to what extent it could modulate the pH of the oral cavity. In light of the known alkalinity-promoting functions of amino acids such as arginine and urea in the oral cavity, it was surprisingly found that compositions comprising serine uniquely possess the ability, in the presence of salivary urea, to lower the pH from an alkaline level (i.e., >7.0) to about neutrality (i.e., about 7.0) or even (depending on arginine concentration) to a slightly acidic level (i.e., <7.0). Thus, serine-containing compositions can be used to counteract some of the undesirable alkalinity generated by the catabolism of urea and other nitrogen-containing entities by bacteria in the oral cavity.

Without wishing to be bound by theory, the addition of a serine-containing composition to saliva provides serine as a "pH-fall" factor, as it causes a reduction in pH when converted from serine to cysteine to pyruvate to lactate by bacteria in the oral cavity. Without wishing to be bound by theory, altering the pH of the oral cavity using such a composition can help promote the dominance of saccharidic microorganisms in subgingival dental plaque over asaccharidic microorganisms, thus reducing the overall accumulation and formation of dental calculus. Such serine-containing compositions are also useful in treating and preventing periodontal disease.

It was found that the effectiveness of such serine-containing compositions can be further improved by the addition of one or more organic mono- or multi-phosphate salts (e.g., a biological salt such as an inositol salt (e.g., an inositol monophosphate salt, an inositol pentaphosphate salt, or an inositol hexaphosphate (a.k.a., phytate) salt such as sodium phytate and potassium phytate). Phytates are phosphate anions with phosphate groups that readily form complexes with calcium ions, complexes easily solubilized in aqueous solutions (e.g., saliva). Without wishing to be bound by theory, the phosphate anions present on phytates and other organic mono- or multi-phosphate salts can serve as carriers in binding to and solubilizing free calcium ions (thereby effectively removing them from saliva) and thus inhibiting the overall accumulation and formation of dental plaque.

pH Response of Exemplary Compositions Containing Amino Acids

As expected, salivary sediment containing 28 mM urea showed a significant rise in pH from neutrality to about 9.0 after 4 hours of incubation at 37° C. (FIG. 1). The pH remained about the same (dropping slightly to 8.8) after 21 hours of incubation at 37° C. In contrast, salivary sediment containing 90 or 120 mM serine in addition to 28 mM urea showed a significantly smaller increase in pH, from neutrality to 8.22 (90 mM serine) or 8.30 (120 mM serine) after 4 hours of incubation at 37° C. After 21 hours of incubation at 37° C., the pH dropped significantly, to 7.85.

In a similar assay, the pH of salivary sediment containing 90 or 120 mM serine, but without urea, dropped from neutrality to about 6.0 after 4 hours of incubation at 37° C., then rose to ~6.6-6.8 after 21 hours of incubation at 37° C.

Unless otherwise specified, all incubation steps described below were at 37° C.

Figure 2:
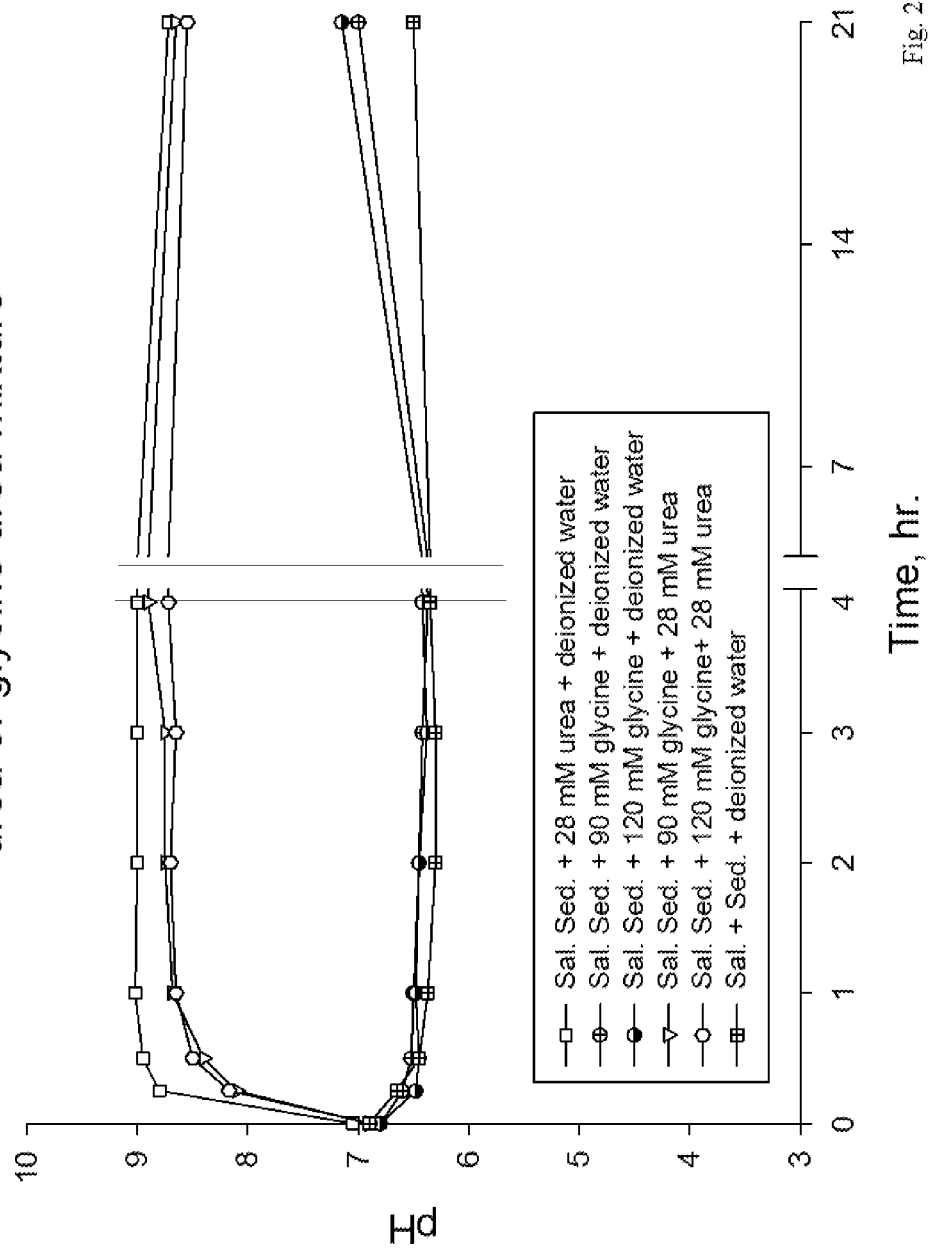
FIG. 2 is a graph showing the pH response of salivary sediment with or without glycine, urea, or a mixture of glycine and urea.

Salivary sediment containing 90 or 120 mM glycine in addition to 28 mM urea showed a rise in pH from neutrality to 8.72 (90 mM glycine) or 8.90 (120 mM glycine) after 4 hours of incubation, falling to 8.65 (90 mM glycine) or 8.55 (120 mM glycine) after 21 hours of incubation. In salivary sediment containing glycine but without urea, the pH fell from 6.80 to ~6.40 after 4 hours of incubation, then rose to ~7.0-7.15 after 21 hours of incubation (FIG. 2).

Figure 3:
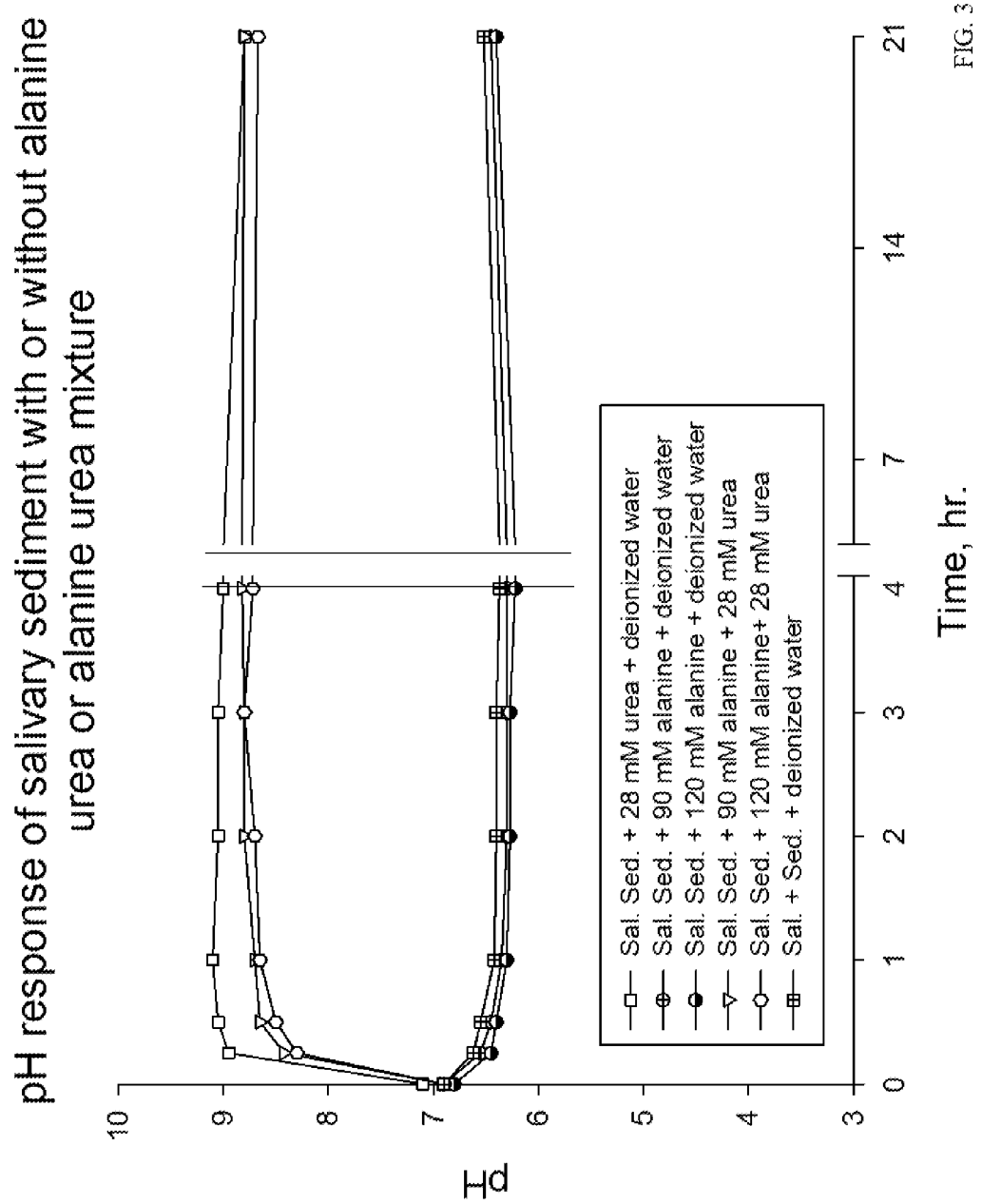
FIG. 3 is a graph showing the pH response of salivary sediment with or without alanine, urea, or a mixture of alanine and urea.

Salivary sediment containing 90 or 120 mM alanine in addition to 28 mM urea showed a rise in pH from neutrality to 8.82 (90 mM alanine) or 8.72 (120 mM alanine) after 4 hours of incubation, falling slightly to 8.80 (90 mM alanine) or 8.67 (120 mM alanine) after 21 hours of incubation. In salivary sediment containing alanine but without urea, the pH fell to 6.30 after 4 hours of incubation, then rose slightly to ~6.4 after 21 hours of incubation (FIG. 3).

Figure 4:
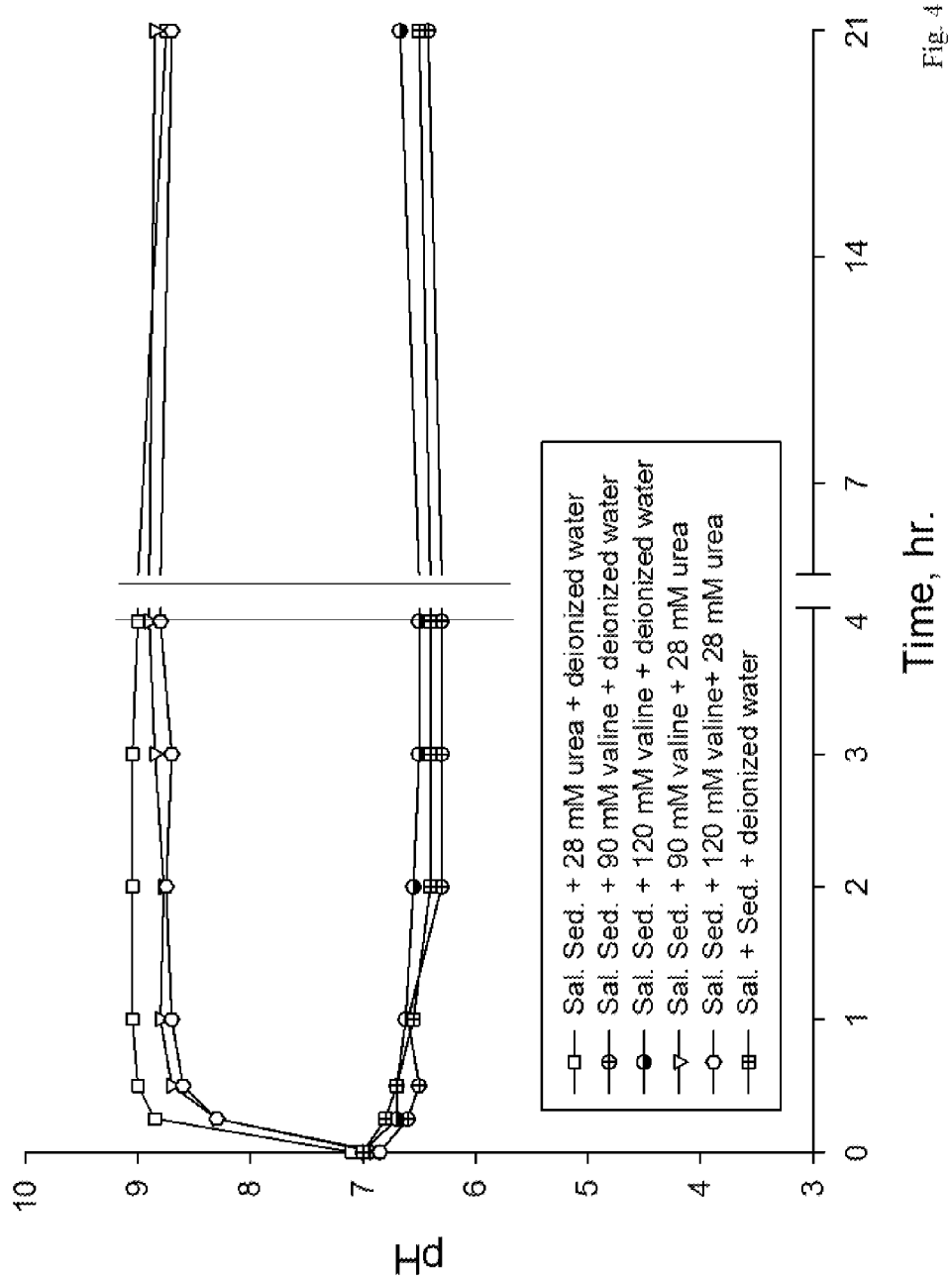
FIG. 4 is a graph showing the pH response of salivary sediment with or without valine, urea, or a mixture of valine and urea.

Salivary sediment containing 90 or 120 mM valine in addition to 28 mM urea showed a rise in pH to 8.90 (90 mM valine) or 8.80 (120 mM valine) after 4 hours of incubation, falling slightly to 8.85 (90 mM valine) or 8.70 (120 mM valine) after 21 hours of incubation. In salivary sediment containing valine but without urea, the pH fell to ~6.3-6.5 after 4 hours of incubation, then rose to ~6.4-6.7 after 21 hours of incubation (FIG. 4).

Figure 5:
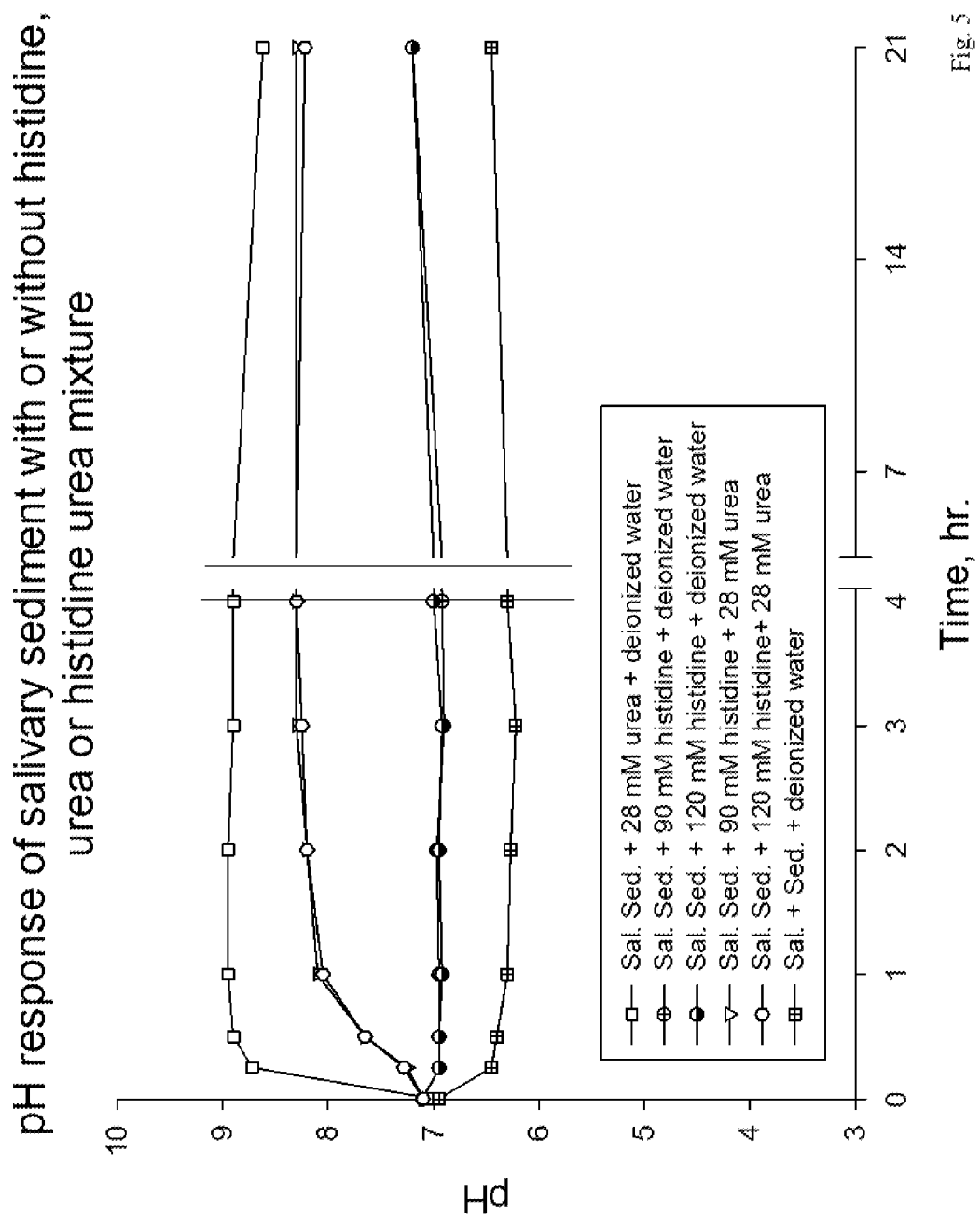
FIG. 5 is a graph showing the pH response of salivary sediment with or without histidine, urea, or a mixture of histidine and urea.

Salivary sediment containing 90 or 120 mM histidine in addition to 28 mM urea showed a rise in pH from neutrality to 8.30 after 4 hours of incubation, remaining at 8.30 (90 mM histidine) or falling slightly to 8.22 (120 mM histidine) after 21 hours of incubation. In salivary sediment containing histidine but without urea, the pH fell to ~6.92-7.00 after 4 hours of incubation, then rose to 7.20 after 21 hours of incubation (FIG. 5).

Figure 6:
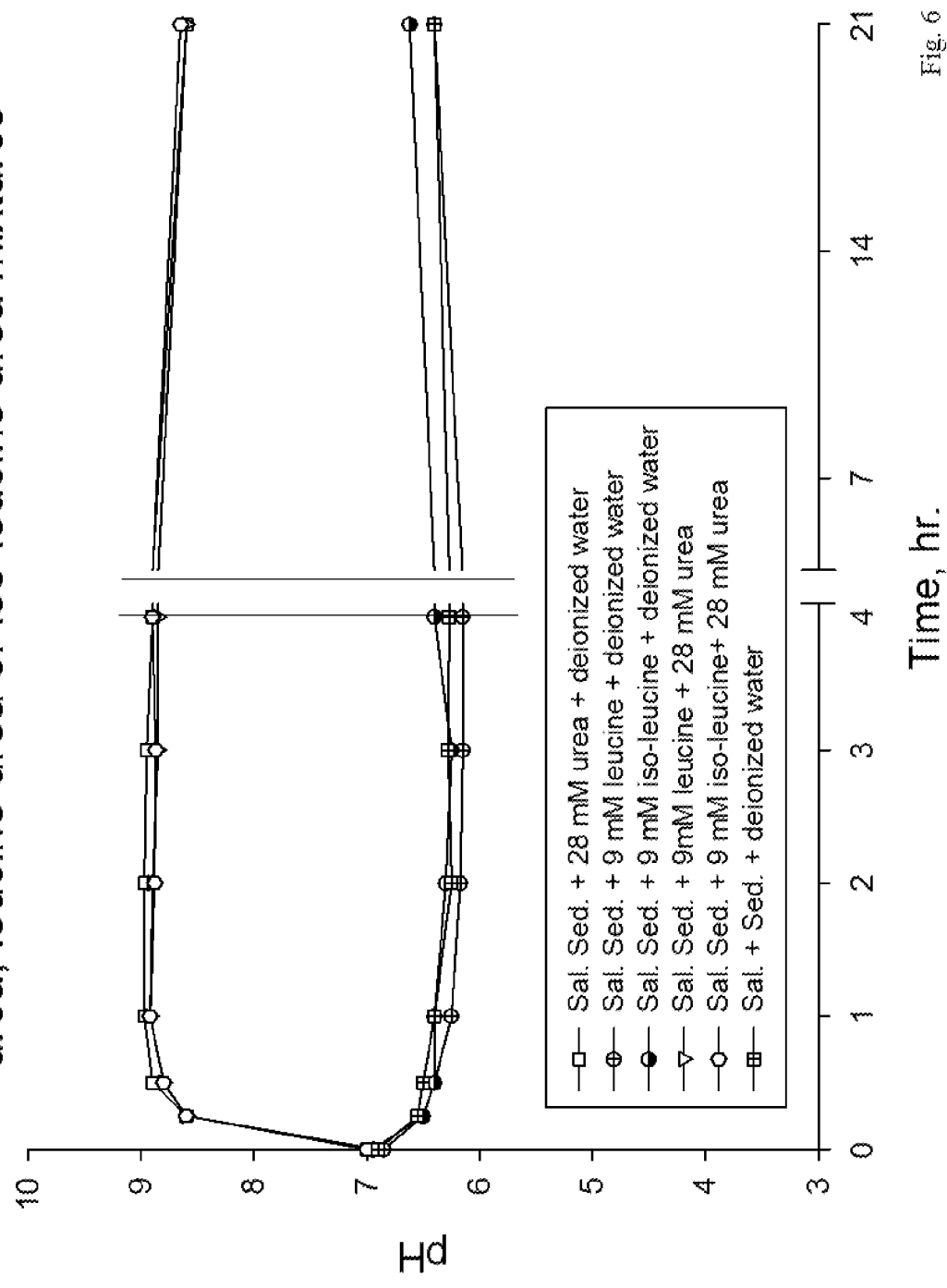
FIG. 6 is a graph showing the pH response of salivary sediment with or without leucine, isoleucine, urea, or a mixture of leucine and urea or isoleucine and urea.

Salivary sediment containing 9 mM leucine in addition to 28 mM urea showed a rise in pH from neutrality to 8.85 after 4 hours of incubation, falling to 8.60 after 21 hours of incubation. Similarly, salivary sediment containing 9 mM isoleucine in addition to 28 mM urea showed a rise in pH from neutrality to 8.90 after 4 hours of incubation, falling to 8.65 after 21 hours of incubation. In salivary sediment containing leucine but without urea, the pH fell to 6.15 after 4 hours of incubation, then rose to 6.40 after 21 hours of incubation. In salivary sediment containing isoleucine but without urea, the pH fell to 6.40 after 4 hours of incubation, then rose to 6.62 after 21 hours of incubation (FIG. 6).

Figure 7:
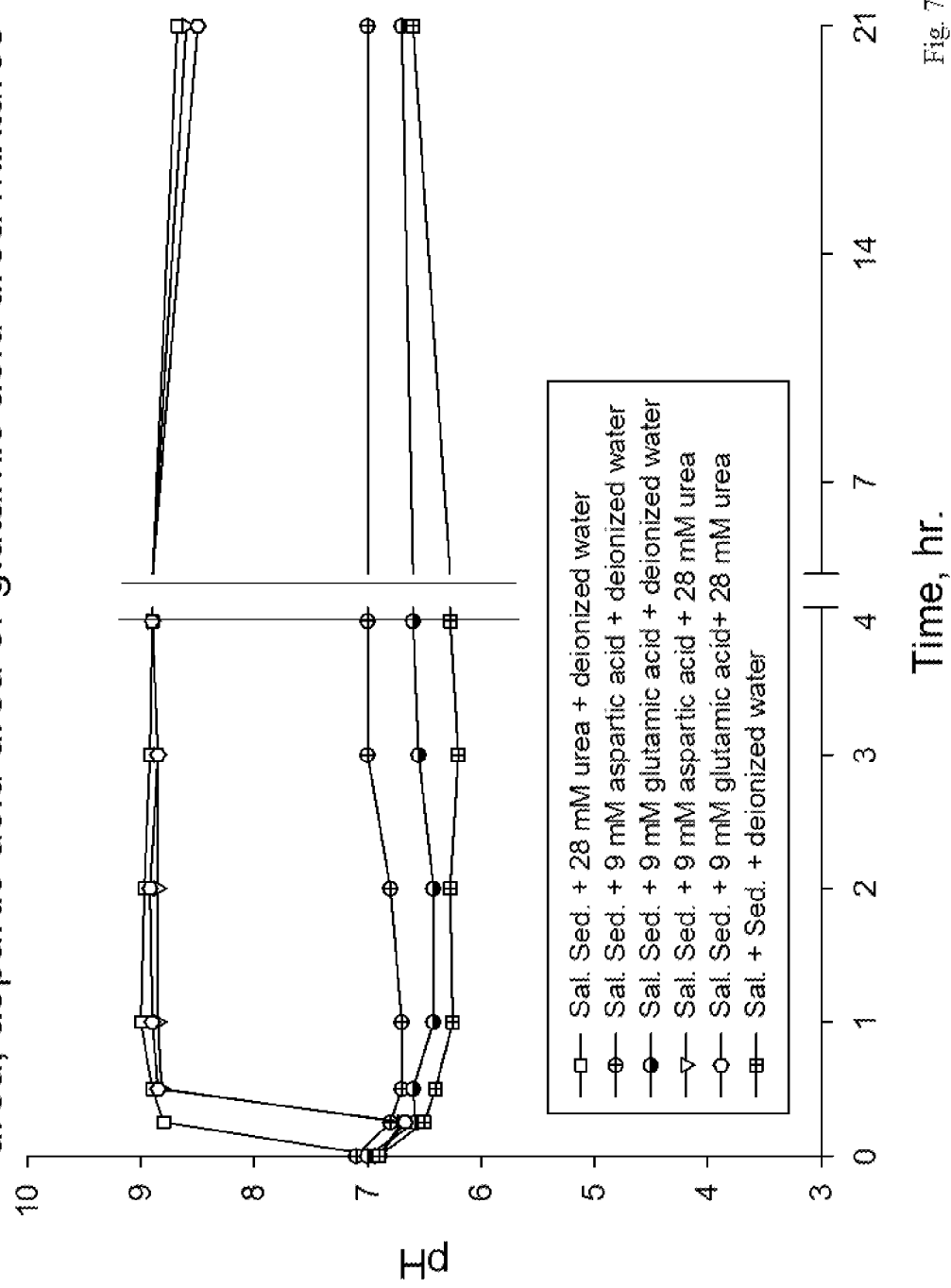
FIG. 7 is a graph showing the pH response of salivary sediment with or without aspartic acid, glutamic acid, urea, or a mixture of aspartic acid and urea or glutamic acid and urea.

Salivary sediment containing 9 mM aspartic acid in addition to 28 mM urea showed a rise in pH to 8.90 after 4 hours of incubation, falling to 8.60 after 21 hours of incubation. Similarly, salivary sediment containing 9 mM glutamic acid in addition to 28 mM urea showed a rise in pH to 8.90 after 4 hours of incubation, falling to 8.50 after 21 hours of incubation. In salivary sediment containing aspartic acid but without urea, the pH remained at 7.00 after overnight incubation. In salivary sediment containing glutamic acid but without urea, the pH fell to 6.70 after overnight incubation (FIG. 7).

Figure 8:
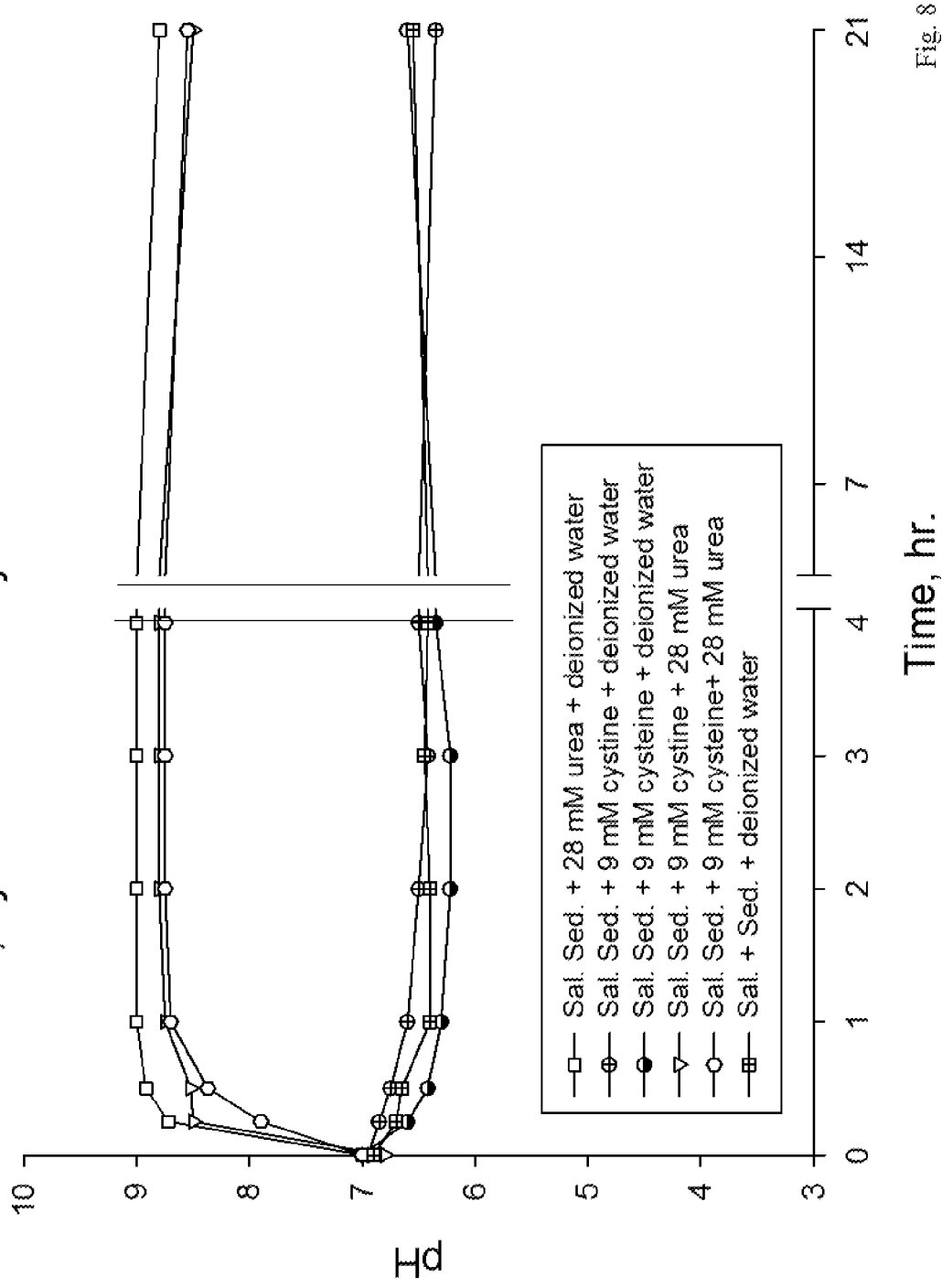
FIG. 8 is a graph showing the pH response of salivary sediment with or without cystine, cysteine, urea, or a mixture of cystine and urea or cysteine and urea.

Salivary sediment containing 9 mM cystine or 9 mM cysteine in addition to 28 mM urea showed a rise in pH to 8.80 (cystine) or 8.75 (cysteine) after 4 hours of incubation, falling to 8.50 (cystine) or 8.55 (cysteine) after 21 hours of incubation. In salivary sediment containing cystine but without urea, the pH fell to 6.35 after overnight incubation. In salivary sediment containing cysteine but without urea, the pH fell to 6.35 after 4 hours of incubation, then rose to 6.60 after 21 hours of incubation (FIG. 8).

Figure 9:
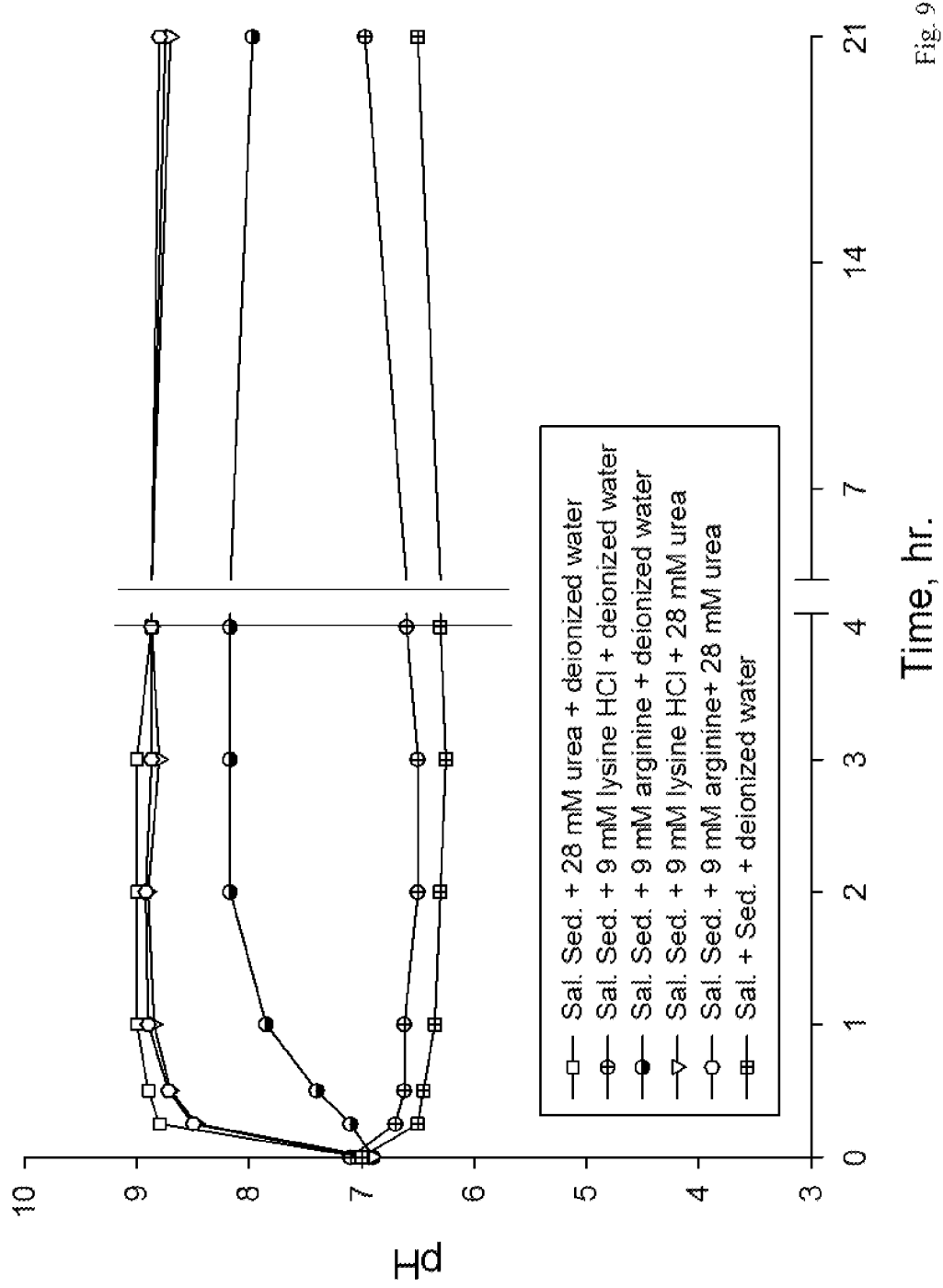
FIG. 9 is a graph showing the pH response of salivary sediment with or without lysine, arginine, urea, or a mixture of lysine and urea or arginine and urea.

Salivary sediment containing 9 mM lysine or 9 mM arginine in addition to 28 mM urea showed a rise in pH to 8.70 (lysine) or 8.80 (arginine) after overnight incubation. In salivary sediment containing lysine but without urea, the pH remained at neutrality after overnight incubation. In salivary sediment containing arginine but without urea, the pH rose to 7.97 after 21 hours of incubation (FIG. 9).

Figure 10:
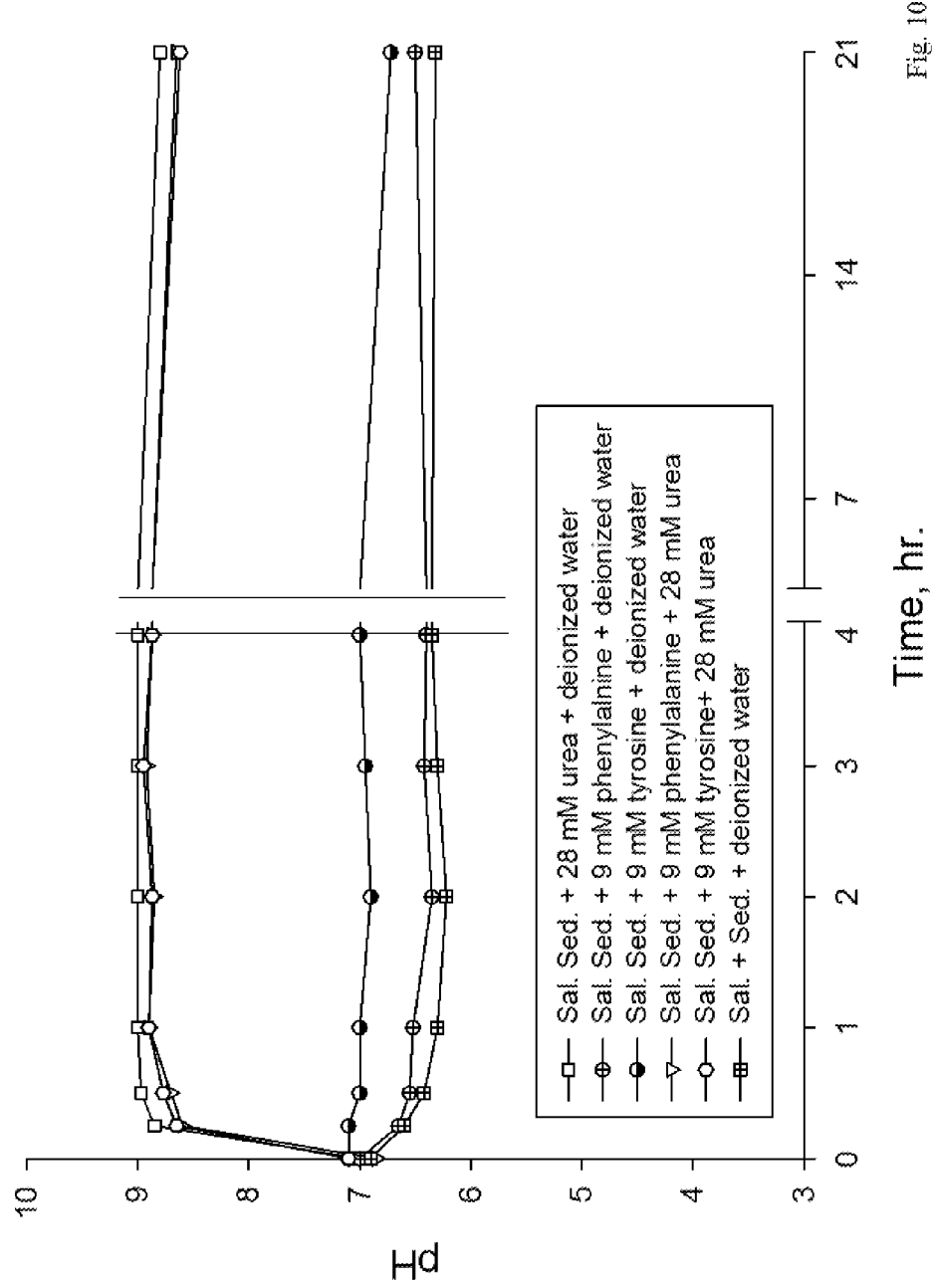
FIG. 10 is a graph showing the pH response of salivary sediment with or without phenylalanine, tyrosine, urea, or a mixture of phenylalanine and urea or tyrosine and urea.

Salivary sediment containing 9 mM phenylalanine or 9 mM tyrosine in addition to 28 mM urea showed a rise in pH to 8.87 after 4 hours of incubation, falling to 8.65 (phenylalanine) or 8.62 (tyrosine) after overnight incubation (FIG. 10).

Figure 11:
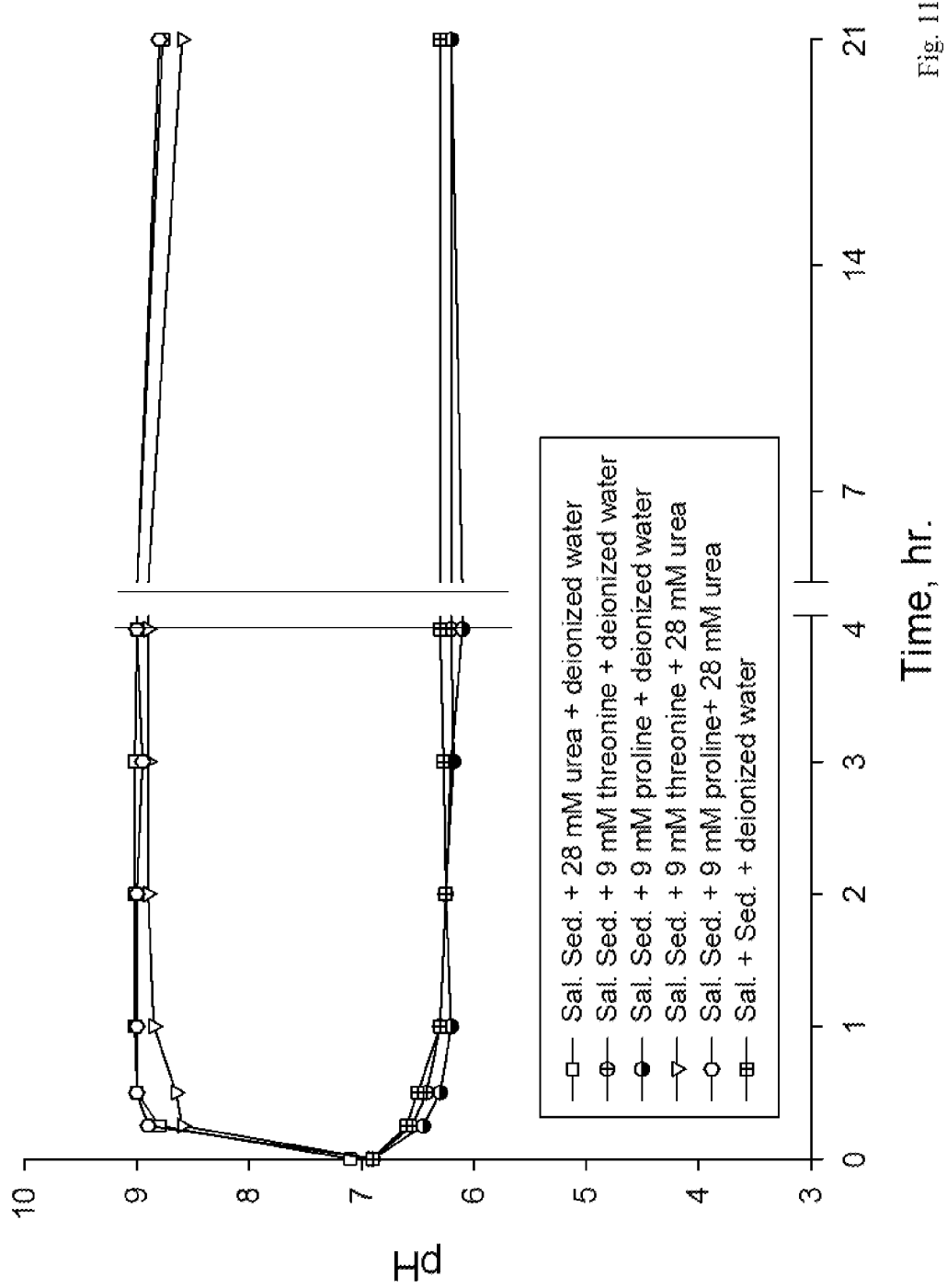
FIG. 11 is a graph showing the pH response of salivary sediment with or without threonine, proline, urea, or a mixture of threonine and urea or proline and urea.

Salivary sediment containing 9 mM threonine or 9 mM proline in addition to 28 mM urea showed a rise in pH to 8.90 (threonine) or 9.00 (proline) after 4 hours of incubation, falling to 8.60 (threonine) or 8.80 (proline) after overnight incubation. In salivary sediment containing threonine or proline but without urea, the pH fell to 6.20 (threonine) or 6.10 (proline) after 4 hours of incubation, then remained about unchanged after 21 hours of incubation (FIG. 11).

Figure 12:
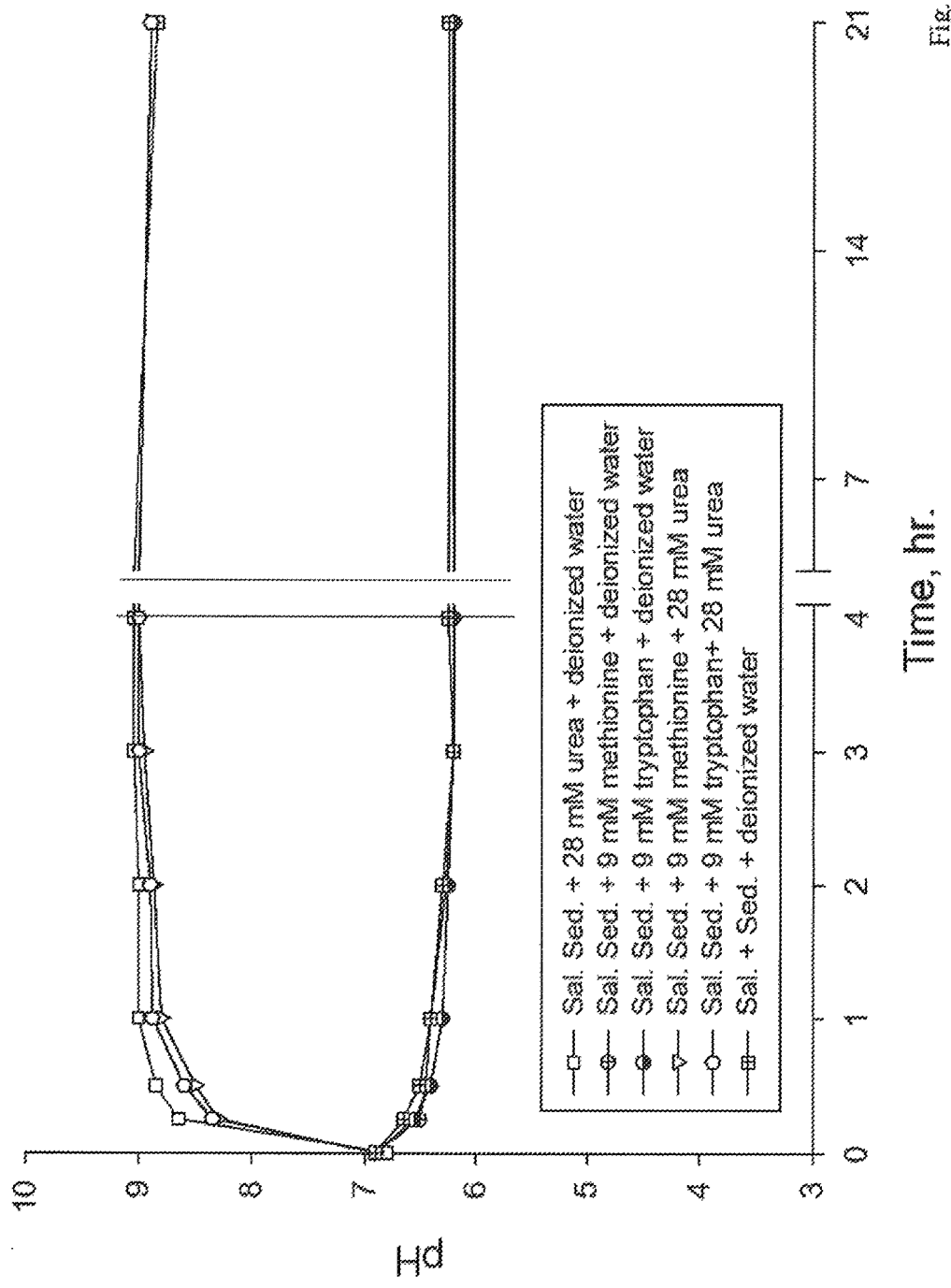
FIG. 12 is a graph showing the pH response of salivary sediment with or without methionine, tryptophan, urea, or a mixture of methionine and urea or tryptophan and urea.

Salivary sediment containing 9 mM methionine or 9 mM tryptophan in addition to 28 mM urea showed a rise in pH to 9.00 after 4 hours of incubation, falling slightly to 8.90 after overnight incubation. In salivary sediment containing methionine or tryptophan but without urea, the pH fell to 6.20 after overnight incubation (FIG. 12).

Figure 13:
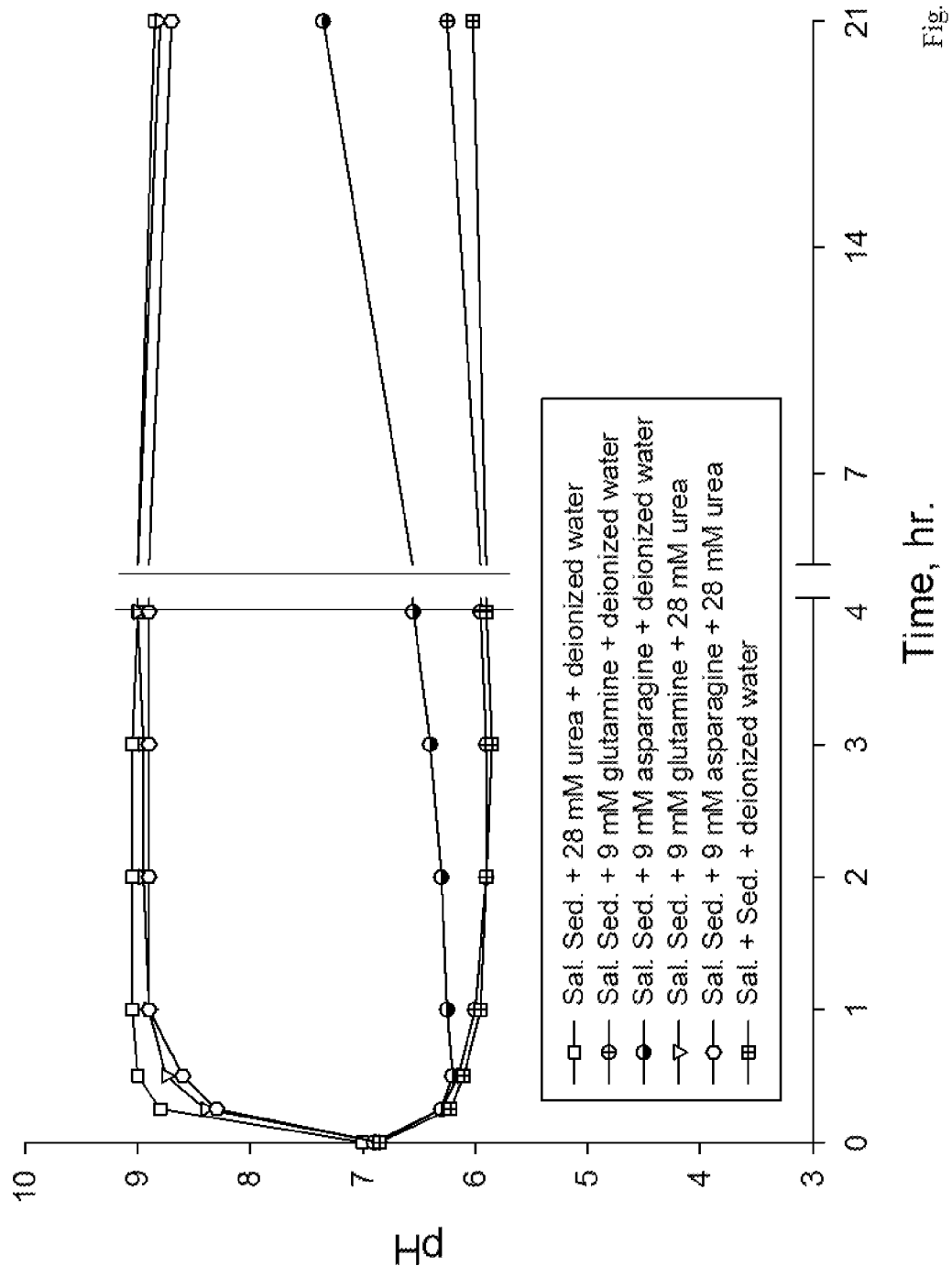
FIG. 13 is a graph showing the pH response of salivary sediment with or without glutamine, asparagine, urea, or a mixture of glutamine and urea or asparagine and urea.

Salivary sediment containing 9 mM glutamine in addition to 28 mM urea showed a rise in pH to 9.00 after 4 hours of incubation, falling to 8.80 after overnight incubation. In salivary sediment containing glutamine but without urea, the pH fell to 5.95 after 4 hours of incubation, then rose to 6.25 after 21 hours of incubation (FIG. 13).

Salivary sediment containing 9 mM asparagine in addition to 28 mM urea showed a rise in pH to 8.90 after 4 hours of incubation, falling to 8.70 after 21 hours of incubation. In salivary sediment containing asparagine but without urea, the pH fell to 6.55 after 4 hours of incubation, then rose to 7.35 after overnight incubation (FIG. 13).

pH Response of Exemplary Serine Compositions Containing Sodium Phytate

Figure 14:
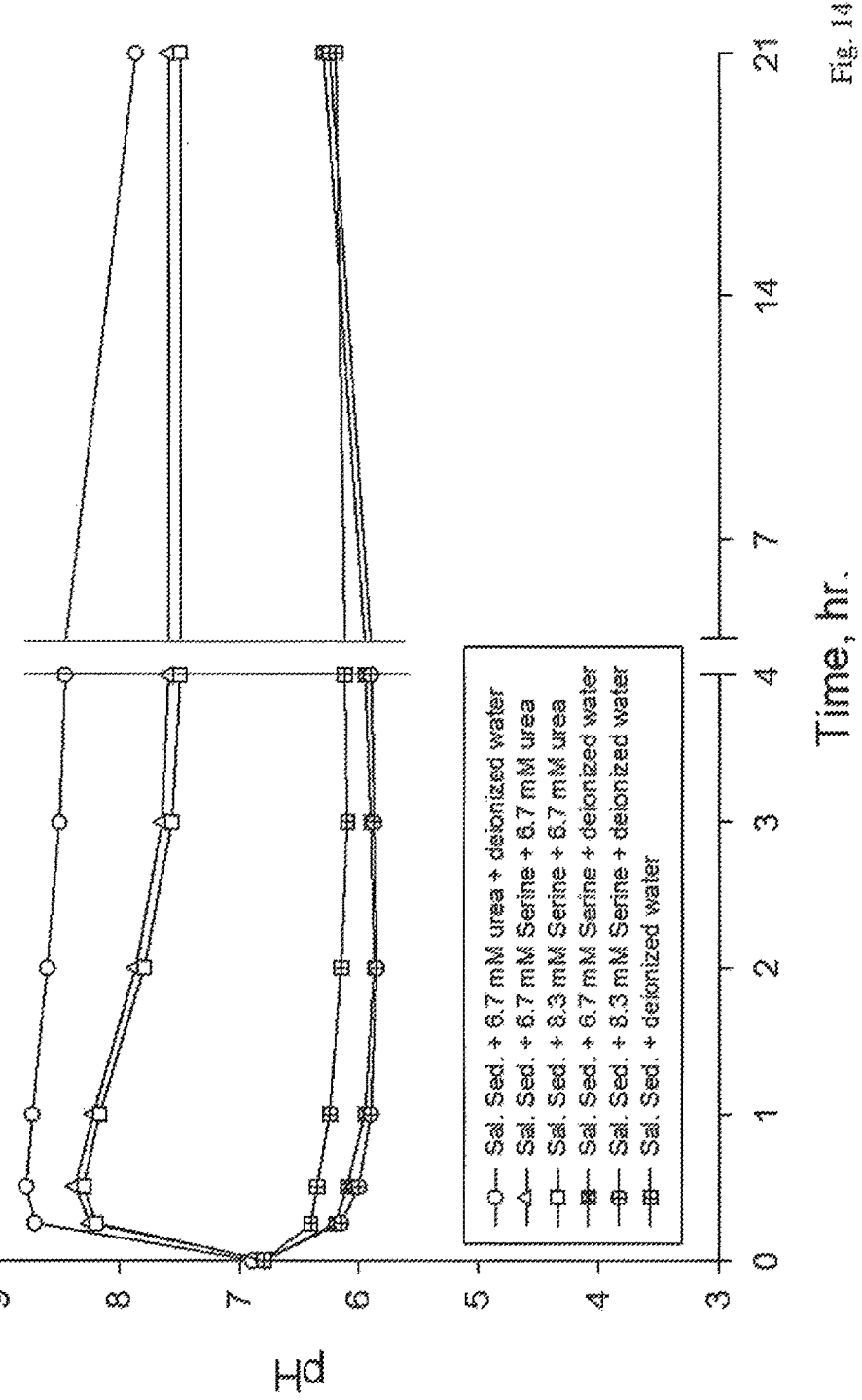
FIG. 14 is a graph showing the pH response of salivary sediment with 6.7 or 8.3 mM serine, with or without urea.

Salivary sediment containing 6.70 mM serine in addition to 6.70 mM urea showed a rise in pH to 7.60 after 21 hours of incubation. In salivary sediment containing 6.70 mM serine but without urea, the pH fell to 5.95 after 4 hours of incubation, then rose to 6.30 after 21 hours of incubation (FIG. 14).

Similarly, salivary sediment containing 8.30 mM serine in addition to 6.70 mM urea showed a rise in pH to 7.50 after 21 hours of incubation. In salivary sediment containing 8.30 mM serine but without urea, the pH fell to 5.90 after 4 hours of incubation, then rose to 6.25 after 21 hours of incubation (FIG. 14).

Figure 15:
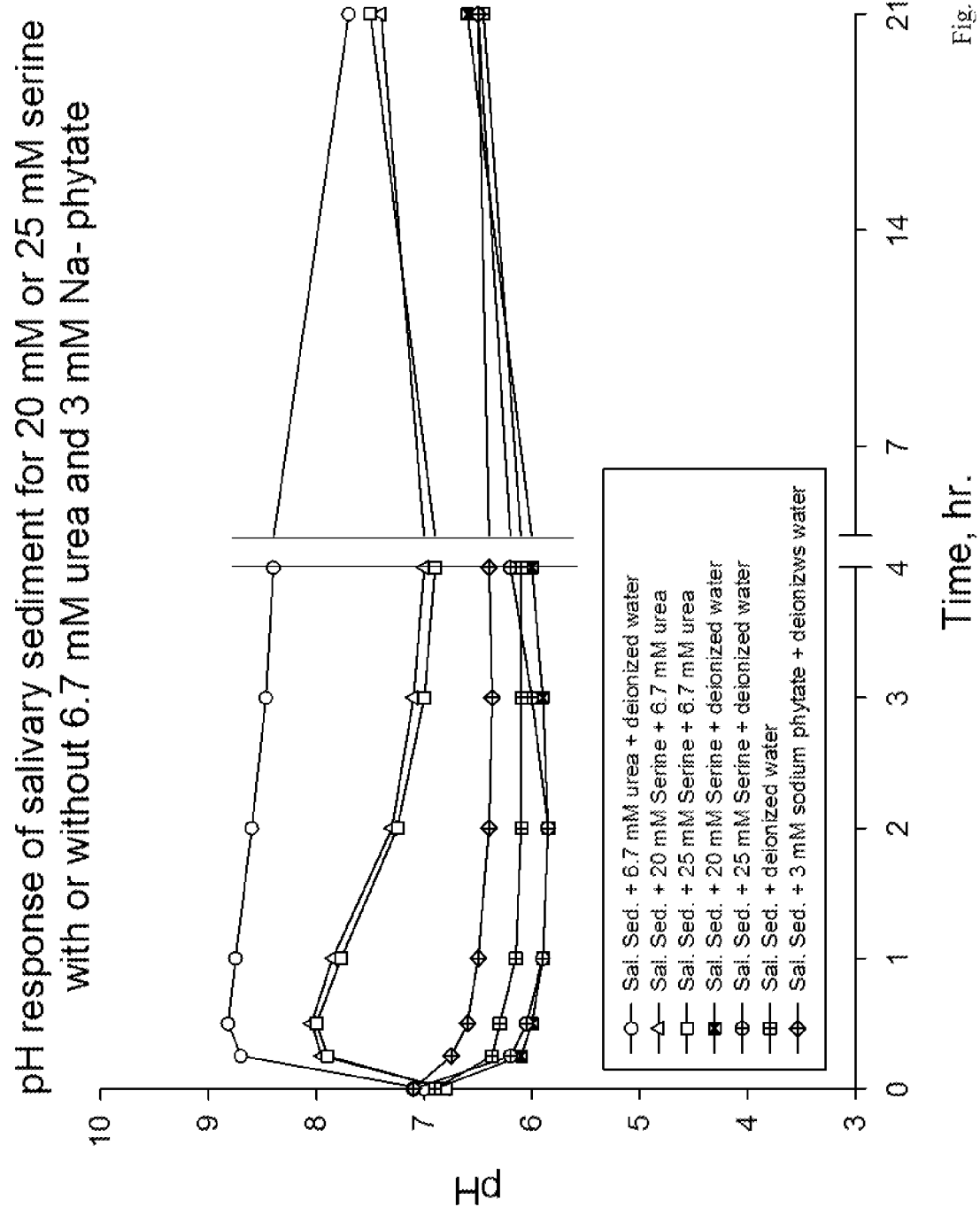
FIG. 15 is a graph showing the pH response of salivary sediment with 20 or 25 mM serine, with or without urea and 3 mM sodium phytate.

The pH of salivary sediment containing 20 mM serine and 3 mM sodium phytate showed very little change from neutrality even with 6.70 mM urea. A similar pH pattern was observed with salivary sediment containing 25 mM serine, 3 mM sodium phytate, and 6.70 mM urea. In the absence of urea, salivary sediment containing 20 mM serine showed a pH drop to 6.20 from an initial pH of 6.90 after 4 hours of incubation; then, at 21 hours, it rose to 6.65. In the absence of urea, salivary sediment containing 25 mM serine showed a pH drop to 6.17 from an initial pH of 7.00 after 4 hours of incubation; then, at 21 hours, it rose to 6.70 (FIG. 15).

Figure 16:
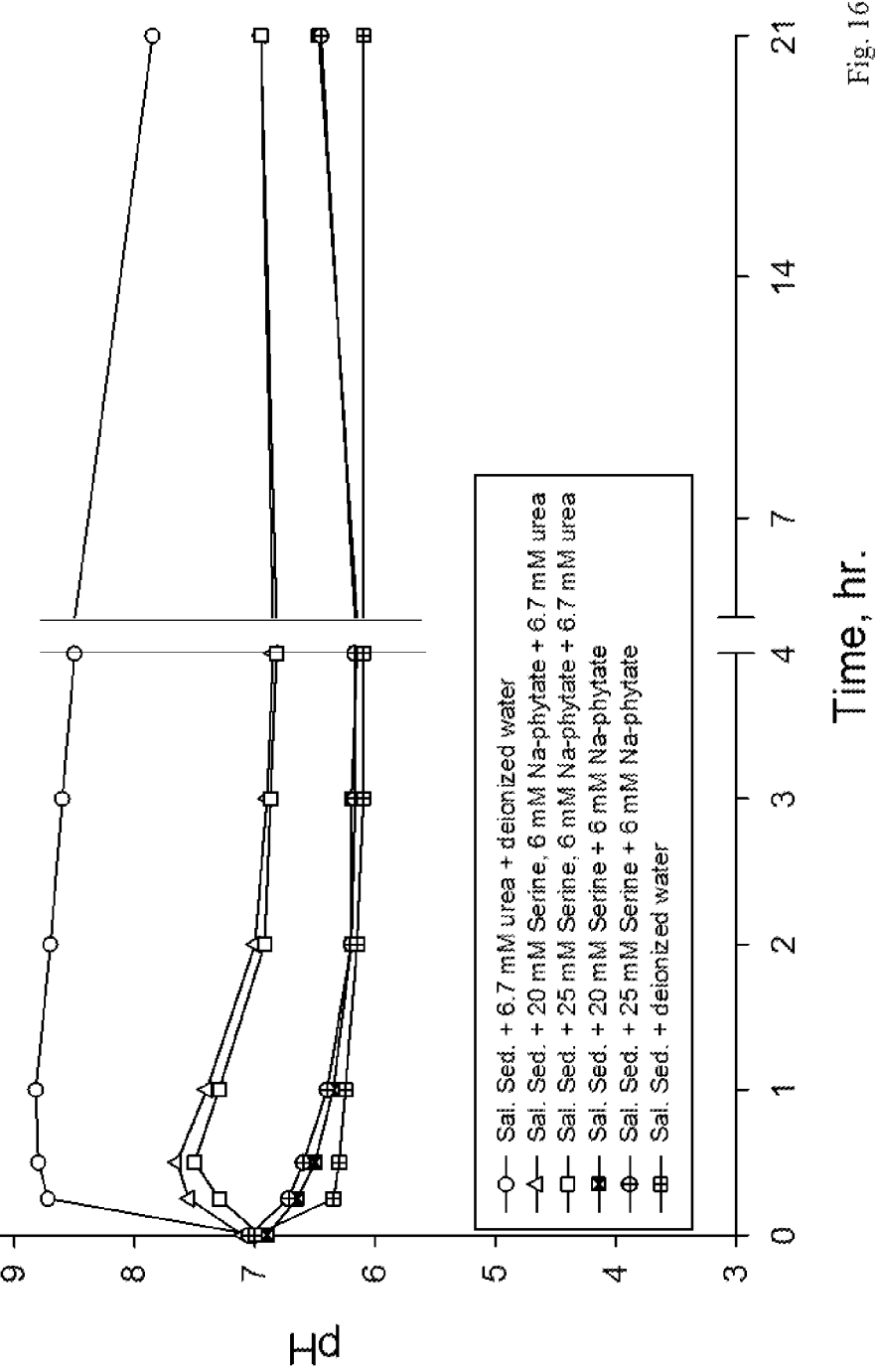
FIG. 16 is a graph showing the pH response of salivary sediment with 20 or 25 mM serine, with or without urea and 6 mM sodium phytate.

The pH of salivary sediment containing 20 or 25 mM serine and 6 mM sodium phytate showed very little change from neutrality even with 6.70 mM urea. In the absence of urea, salivary sediment containing 20 mM serine showed a pH drop to 7.15 (and salivary sediment containing 25 mM serine showed a pH drop to 6.17) after 4 hours of incubation; then, at 21 hours, it rose to 6.47 (20 mM serine) or 6.45 (25 mM serine) (FIG. 16).

Figure 17:
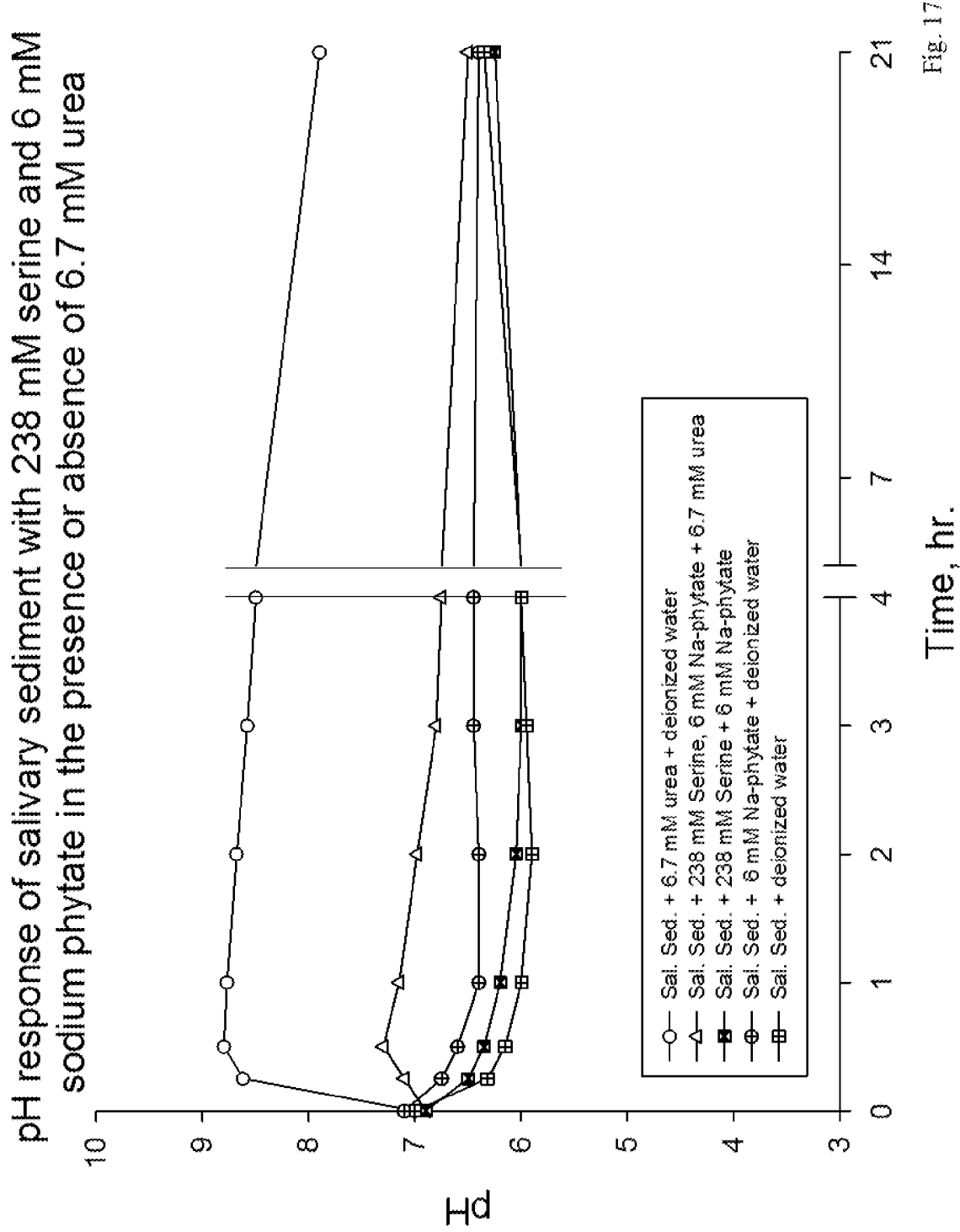
FIG. 17 is a graph showing the pH response of salivary sediment with 238 mM serine, with or without urea and 6 mM sodium phytate.

The pH of salivary sediment containing 238 mM serine and 6 mM sodium phytate in addition to 6.70 mM urea showed a small rise in pH at the early stages of incubation, and dropped to 6.50 by 21 hours of incubation. In the absence of urea, the pH dropped to 6.00 after 4 hours of incubation; then, at 21 hours, it rose to 6.25 (FIG. 17).

pH and Calcium Levels of Exemplary Compositions Incubated with Tooth Enamel

Figure 18:
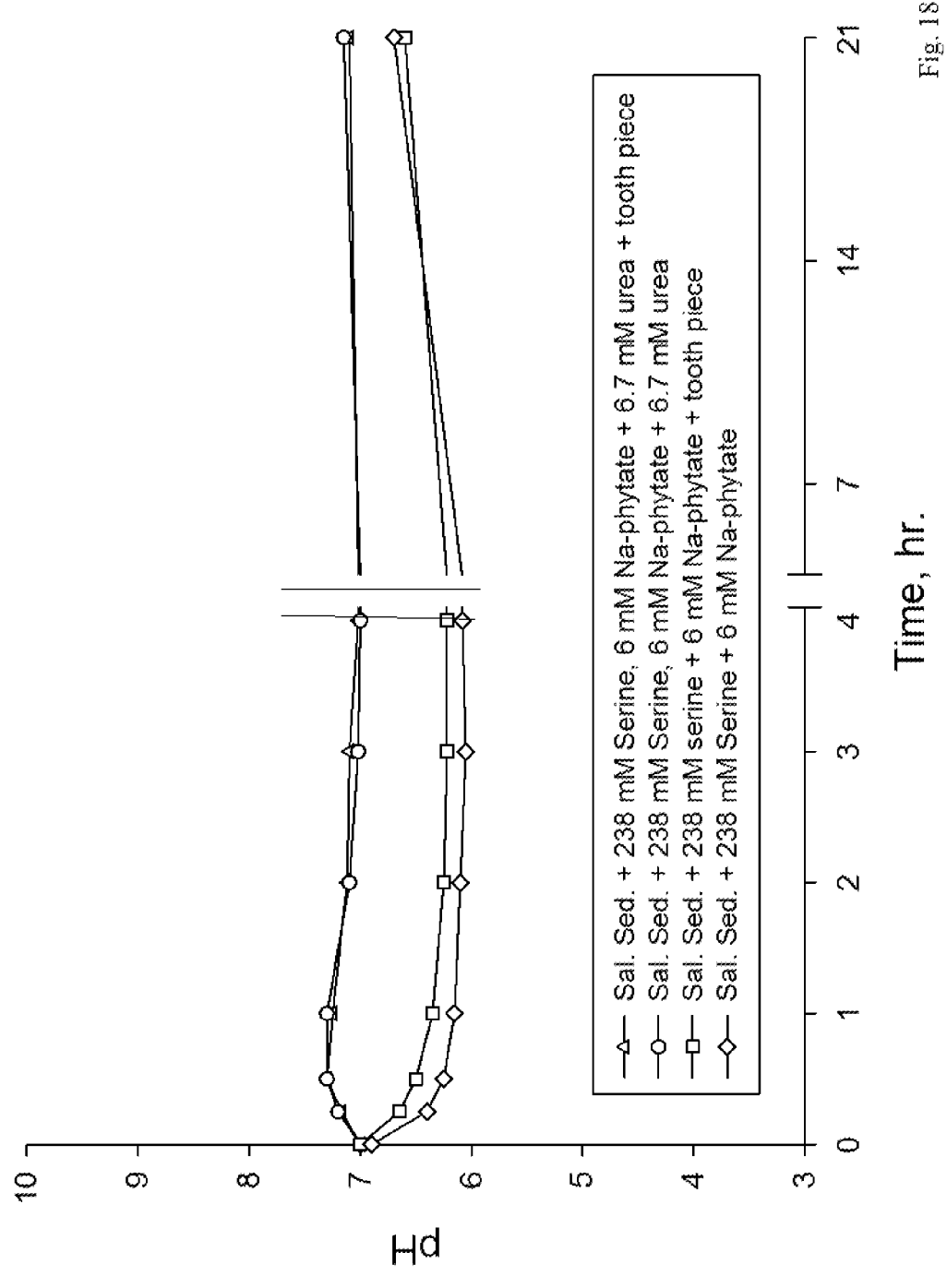
FIG. 18 is a graph showing the pH response of salivary sediment with 238 mM serine and 6 mM sodium phytate, with or without urea and a piece of human tooth.

When a small block of tooth substance with only enamel exposed (FIGS. 18 and 23) was incubated with a composition containing 238 mM serine, 6 mM sodium phytate, and 6.7 mM urea, the resulting mixtures showed a rise in pH to 7.30 from 7.00 at the early stages of incubation, and a drop in pH thereafter to 7.10. The pH profile of exactly the same incubation mixture without the tooth block added was more or less the same as the pH profile when the tooth block was present. In the absence of urea, with or without exposed enamel from a piece of tooth (FIG. 23), the incubation showed a pH fall for a period of four hours, which was then followed by a significant rise after overnight incubation (FIG. 18).

Figure 19:
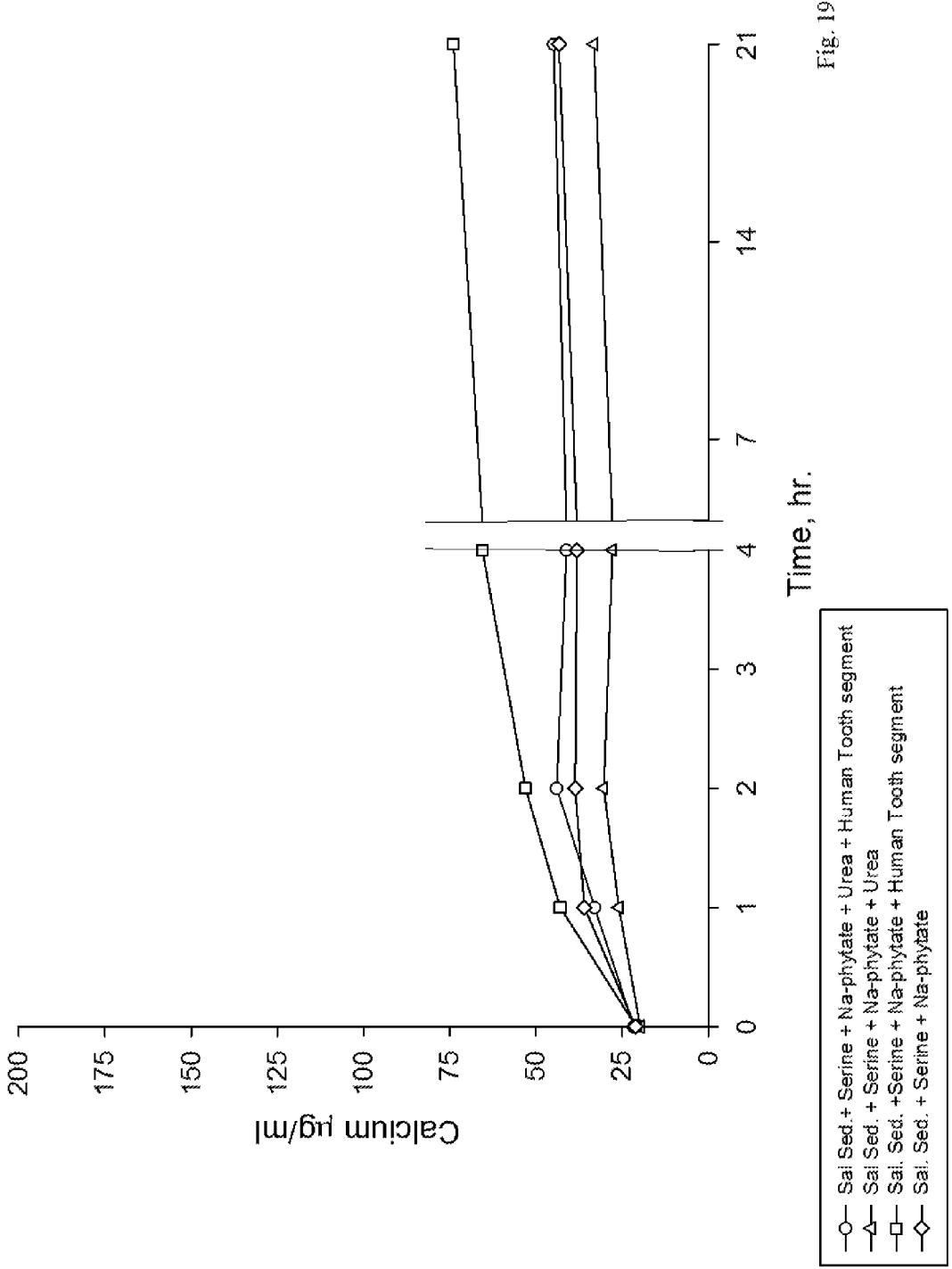
FIG. 19 is a graph showing calcium release in an incubation mixture containing salivary sediment, serine, sodium phytate, and urea, with or without enamel from a human tooth.

The initial supernatant calcium level was 21.58 μg/ml for the mixture containing serine, sodium phytate, urea, and exposed enamel of a tooth piece, which gradually rose to 44.80 μg/ml after overnight incubation. The same incubation mixture without the exposed enamel of a tooth piece showed an initial supernatant calcium level of 19.74 μg/ml, which gradually rose to 33.11 μg/ml by the end of the incubation. In the absence of urea in the incubation mixture containing serine, sodium phytate, and exposed enamel of a tooth piece, the initial supernatant calcium level was 20.15 μg/ml, which rose to 73.87 μg/ml after 21 hours of incubation. In the absence of urea and the absence of exposed enamel of a tooth piece, the incubation mixture containing serine and sodium phytate showed an initial supernatant calcium level of 21.08 μg/ml, which rose to 43.30 μg/ml at the end of the incubation (FIG. 19).

pH and Calcium Levels of Exemplary Compositions Incubated with Tooth Cementum

Figure 20:
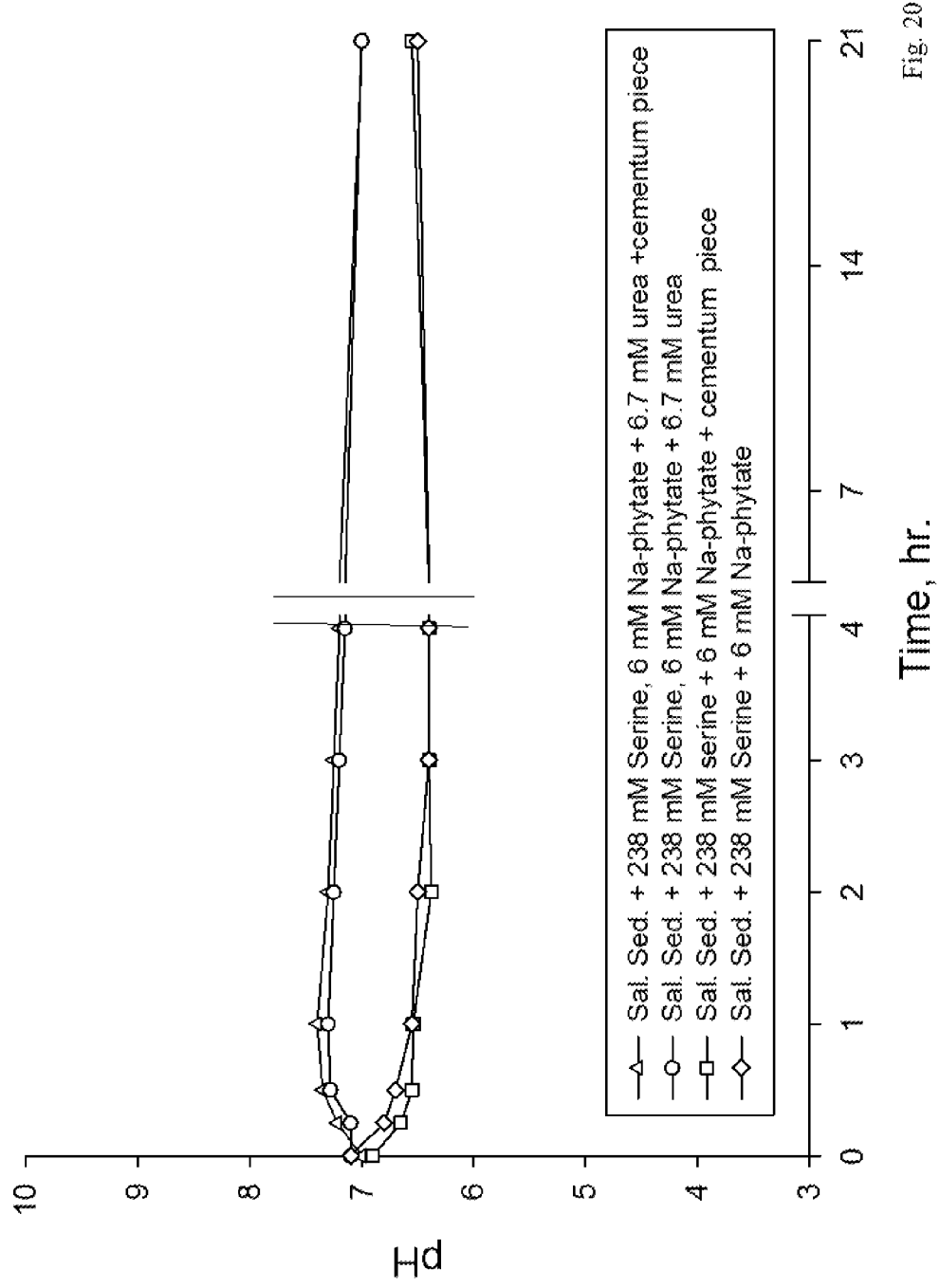
FIG. 20 is a graph showing the pH response of salivary sediment with 238 mM serine and 6 mM sodium phytate, with or without urea and a piece of human tooth cementum.
Figure 24:
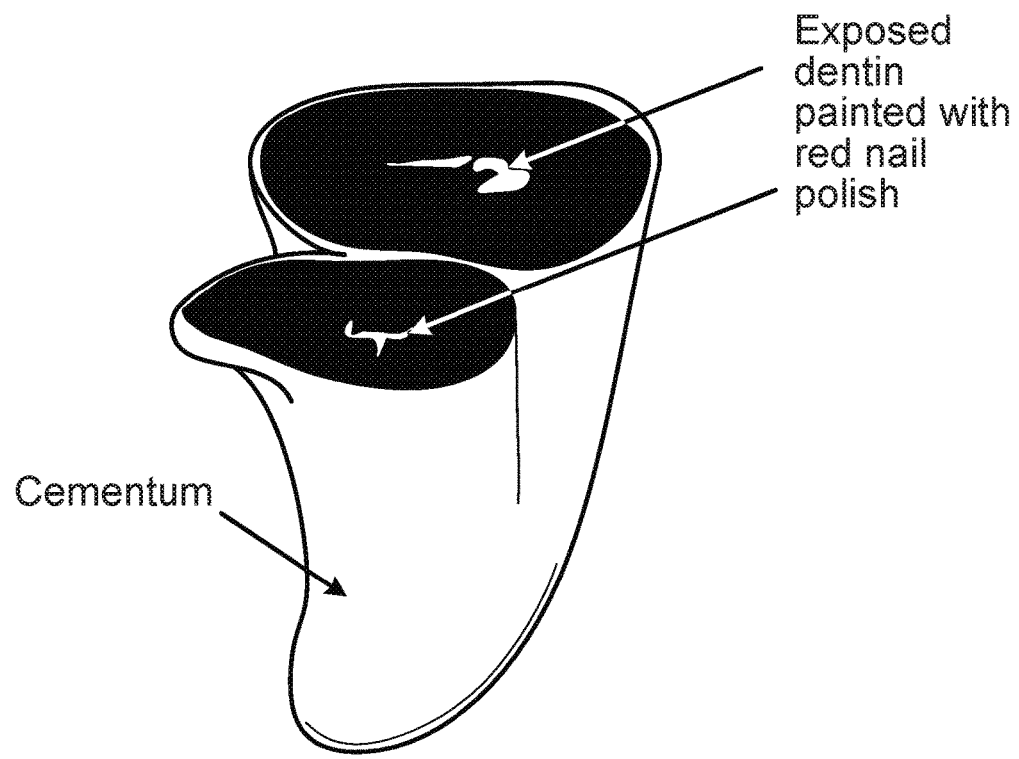
FIG. 24 is a photograph showing the roots of a molar tooth.

Mixtures containing an exposed piece of tooth cementum (FIG. 24), plus serine, sodium phytate, and urea, showed a pH profile of a slow rise from neutrality and a slow fall back to neutrality at the end of the incubation period. A similar pH pattern was observed for the same incubation mixture without the presence of the exposed piece of tooth cementum. In the absence of urea, mixtures containing an exposed piece of tooth cementum, plus serine and sodium phytate, showed a pH drop to 6.40 after 4 hours of incubation, then a rise to 6.55 after 21 hours of incubation. A similar pH pattern was observed for mixtures without both urea and an exposed piece of tooth cementum (FIG. 20).

Figure 21:
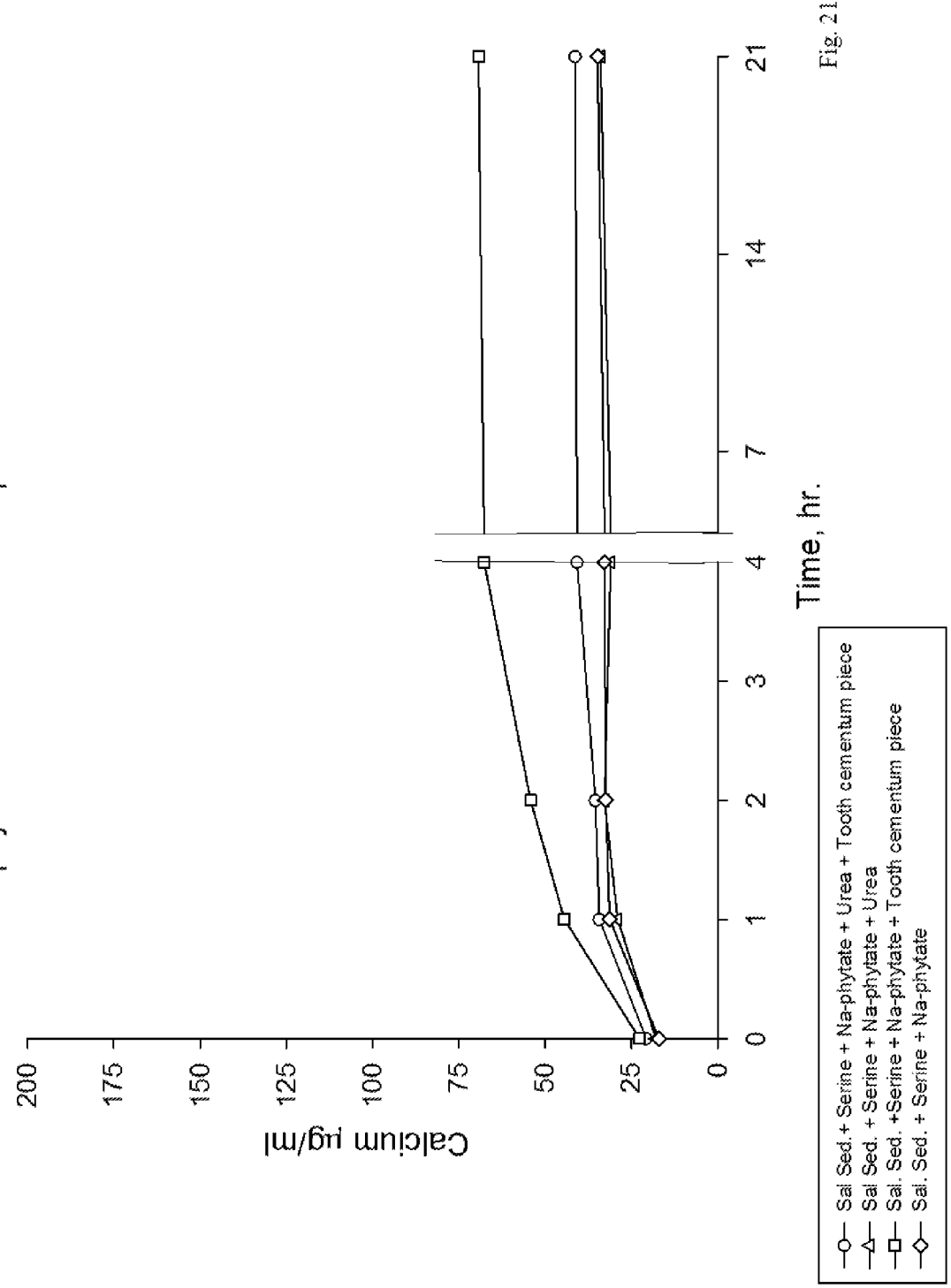
FIG. 21 is a graph showing calcium release in an incubation mixture containing salivary sediment, serine, sodium phytate, and urea, with or without cementum from a human tooth.

The initial supernatant calcium level was 20.65 μg/ml for the mixture containing serine, sodium phytate, urea, and exposed cementum of a tooth piece, which rose to 41.30 μg/ml after 21 hours of incubation. The same incubation mixture without the exposed tooth cementum showed an initial supernatant calcium level of 17.83 μg/ml, which rose to 33.94 μg/ml by the end of the incubation. In the absence of urea in the incubation mixture containing serine, sodium phytate, and exposed cementum of a tooth piece, the initial supernatant calcium level was 22.65 μg/ml, which rose to 69.31 μg/ml after 21 hours of incubation. In the absence of urea and the absence of exposed cementum of a tooth piece, the incubation mixture containing serine and sodium phytate showed an initial supernatant calcium level of 17.00 μg/ml, which rose to 34.77 μg/ml at the end of the incubation (FIG. 21).

Figure 22:
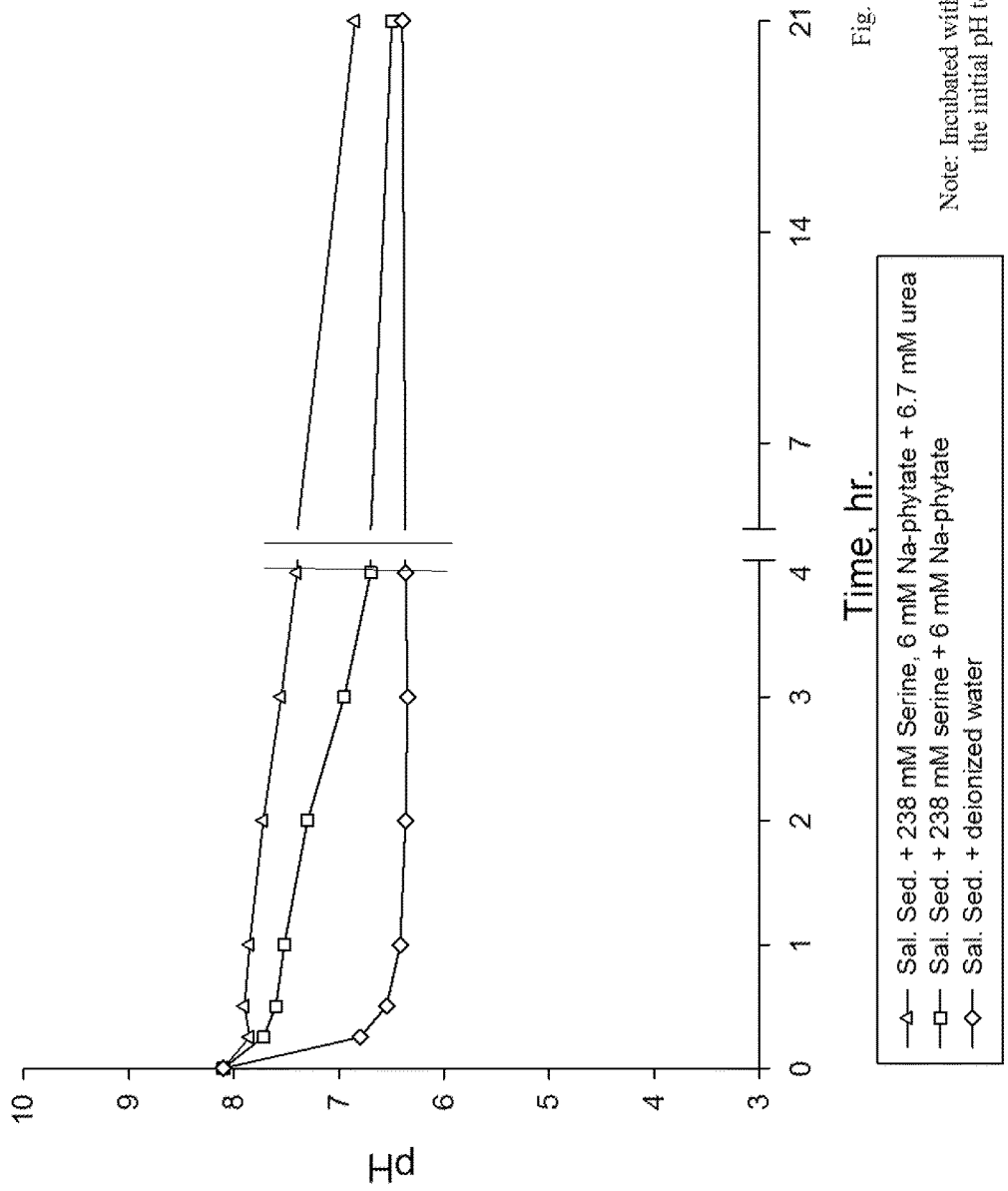
FIG. 22 is a graph showing the pH response of salivary sediment with 238 mM serine and 6 mM sodium phytate, with or without urea, when the initial pH was not adjusted to neutrality.

When the initial pH of the incubation mixture containing salivary sediment, serine, and urea was not adjusted to pH 7.00 before incubation, the initial pH was 8.10, and the pH gradually fell to 6.85 by the end of the incubation. The same pH drop was observed in the absence of urea, except that the pH fell to 6.50 from an initial pH of 8.10 after 21 hours (FIG. 22).

Pharmaceutical Compositions

In some aspects, the compositions and methods described herein include the manufacture and use of pharmaceutical compositions and medicaments that include one or more bivalent compounds as disclosed herein. Also included are the pharmaceutical compositions themselves.

In some aspects, the compositions disclosed herein can include other compounds, drugs, or agents used for the treatment of plaque and/or periodontal disease. For example, in some instances, pharmaceutical compositions disclosed herein can be combined with one or more (e.g., one, two, three, four, five, or less than ten) compounds. When co-administered, serine- and phosphate salt-containing compositions disclosed herein can operate in conjunction with other agents used for the treatment of plaque and/or periodontal disease to produce mechanistically additive or synergistic therapeutic effects.

In some aspects, the pH of the compositions disclosed herein can be adjusted with pharmaceutically acceptable acids, bases, or buffers. The pH of the compositions disclosed herein is optimally in the range of about 6.0 to about 9.5, preferably in the range of about 6.1 to about 7.0 (e.g., about 6.1 to about 6.3 or about 6.7 to about 7.0).

Pharmaceutical compositions typically include a pharmaceutically acceptable carrier, adjuvant, or vehicle. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. A pharmaceutically acceptable carrier, adjuvant, or vehicle is a composition that can be administered to a patient, together with a compound of the invention, and which does not destroy the pharmacological activity thereof and is nontoxic when administered in doses sufficient to deliver a therapeutic amount of the compound. Exemplary conventional nontoxic pharmaceutically acceptable carriers, adjuvants, and vehicles include saline, solvents, dispersion media, coatings, antibacterial and antifungal agents, isotonic and absorption delaying agents, and the like, compatible with pharmaceutical administration.

In particular, pharmaceutically acceptable carriers, adjuvants, and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β, and γ-cyclodextrin, may also be advantageously used to enhance delivery of compounds of the formulae described herein.

As used herein, the serine- and phosphate salt-containing compositions disclosed herein are defined to include pharmaceutically acceptable derivatives or prodrugs thereof. A "pharmaceutically acceptable derivative" means any pharmaceutically acceptable salt, solvate, or prodrug, e.g., carbamate, ester, phosphate ester, salt of an ester, or other derivative of a compound or agent disclosed herein, which upon administration to a recipient is capable of providing (directly or indirectly) a compound described herein, or an active metabolite or residue thereof. Preferred derivatives and prodrugs include derivatives where a group that enhances aqueous solubility is appended to the structure of formulae described herein. Such derivatives are recognizable to those skilled in the art without undue experimentation. Nevertheless, reference is made to the teaching of Burger's Medicinal Chemistry and Drug Discovery, 5$^{th}$ Edition, Vol. 1: Principles and Practice, which is incorporated herein by reference to the extent of teaching such derivatives.

The serine- and phosphate salt-containing compositions disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated derivative thereof.

In particular, pharmaceutically acceptable salts of serine- and phosphate salt-containing compositions disclosed herein include, e.g., those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalene-sulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include, e.g., alkali metal (e.g., sodium), alkaline earth metal (e.g., magnesium), ammonium and N-(alkyl)4+ salts. The invention also envisions the quaternization of any basic nitrogen-containing groups of the serine- and phosphate salt-containing compositions disclosed herein. Water or oil-soluble or dispersible products can be obtained by such quaternization.

In some aspects, the pharmaceutical compositions disclosed herein can include an effective amount of serine and/or one or more phosphate salts. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment or prevention of plaque or periodontal disease). In some aspects, pharmaceutical compositions can further include one or more additional compounds, drugs, or agents used for the treatment of plaque and/or periodontal disease in amounts effective for causing an intended effect or physiological outcome (e.g., treatment or prevention of plaque or periodontal disease).

Administration of Pharmaceutical Compositions

The pharmaceutical compositions disclosed herein can be formulated or adapted for administration to a subject via any oral route, e.g., any oral route approved by the Food and Drug Administration (FDA). Exemplary methods are described in the FDA Data Standards Manual (DSM) (available at http://www.fda.gov/Drugs/DevelopmentApproval-Process/FormsSubmissionRequirements/ElectronicSubmissions/DataStandardsManualmonographs).

For example, pharmaceutical compositions of this invention can be orally administered in any orally acceptable dosage form including, but not limited to, capsules, tablets (e.g., confections such as (soft) chewable tablets), emulsions and aqueous suspensions, dispersions, pastes or powders (e.g., dentifrices or toothpastes), gums (e.g., chewing gums), and solutions (e.g., mouthwashes or other rinses). In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase combined with emulsifying or suspending agents. If desired, certain sweetening, flavoring, or coloring agents can be added.

In some aspects, an effective dose of a pharmaceutical composition of this invention can include, but is not limited to, e.g., about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, or 3-10,000 mg/kg/day serine and/or one or more phosphate salts, or according to the requirements of the particular pharmaceutical composition.

When the pharmaceutical compositions disclosed herein include a combination of a serine- and phosphate salt-containing composition described herein and one or more additional compounds (e.g., one or more additional compounds, drugs, or agents used for the treatment of plaque and/or periodontal disease), both the compound and the additional compound should be present at dosage levels of between about 1 to 100%, and more preferably between about 5 to 95% of the dosage normally administered in a monotherapy regimen. The additional agents can be administered separately, as part of a multiple dose regimen, from the compounds of this invention. Alternatively, those agents can be part of a single dosage form, mixed together with the compounds of this invention in a single composition.

In some aspects, the pharmaceutical compositions disclosed herein can be included in a container, pack, or dispenser together with instructions for administration.

Methods of Treatment

The methods disclosed herein contemplate administration of an effective amount of a compound or composition to achieve the desired or stated effect. Typically, the compounds or compositions of the invention will be administered from about 1 to about 6 times per day. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Alternatively, such preparations can contain from about 20% to about 80% active compound.

In some aspects, the present disclosure provides methods for using a composition comprising serine and/or one or more phosphate salts, including pharmaceutical compositions (indicated below as 'X') disclosed herein in the following methods:

Substance X for use as a medicament in the treatment of one or more diseases or conditions disclosed herein (e.g., plaque, referred to in the following examples as 'Y'). Use of substance X for the manufacture of a medicament for the treatment of Y; and substance X for use in the treatment of Y.

In some aspects, the methods disclosed include the administration of a therapeutically effective amount of one or more of the compounds or compositions described herein to a subject (e.g., a mammalian subject, e.g., a human subject) who is in need of, or who has been determined to be in need of, such treatment. In some aspects, the methods disclosed include selecting a subject and administering to the subject an effective amount of one or more of the compounds or compositions described herein, and optionally repeating administration as required for the prevention or treatment of plaque and/or periodontal disease.

In some aspects, subject selection can include obtaining a sample from a subject (e.g., a candidate subject) and testing the sample for an indication that the subject is suitable for selection. In some aspects, the subject can be confirmed or identified, e.g. by a health care professional, as having had or having a condition or disease (e.g., periodontal disease). In some aspects, suitable subjects include, for example, subjects who have or had a condition or disease but that resolved the disease or an aspect thereof, present reduced symptoms of disease (e.g., relative to other subjects (e.g., the majority of subjects) with the same condition or disease), or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some aspects, exhibition of a positive immune response towards a condition or disease can be made from patient records, family history, or detecting an indication of a positive immune response. In some aspects, multiple parties can be included in subject selection. For example, a first party can obtain a sample from a candidate subject and a second party can test the sample. In some aspects, subjects can be selected or referred by a medical practitioner (e.g., a general practitioner). In some aspects, subject selection can include obtaining a sample from a selected subject and storing the sample or using the sample in the methods disclosed herein. Samples can include, e.g., plaque or saliva.

In some aspects, methods of treatment can include a single administration, multiple administrations, and repeating administration of one or more compounds disclosed herein as required for the prevention or treatment of the disease or condition from which the subject is suffering (e.g., periodontal disease). In some aspects, methods of treatment can include assessing a level of disease in the subject prior to treatment, during treatment, or after treatment. In some aspects, treatment can continue until a decrease in the level of disease in the subject is detected.

The term "subject," as used herein, refers to any animal. In some instances, the subject is a mammal. In some instances, the term "subject," as used herein, refers to a human (e.g., a man, a woman, or a child).

The terms "administer," "administering," or "administration," as used herein, refer to orally administering a compound or composition, regardless of form. For example, the methods disclosed herein include administration of an effective amount of a compound or composition to achieve the desired or stated effect. The pharmaceutical compositions disclosed herein can optionally be administered to the oral cavity or specific portions of the oral cavity (e.g., one or more teeth, or one or more portions of one or more teeth (e.g., exposed enamel, dentine, or cementum)) using one or more devices known in the art, e.g., brushes (e.g., toothbrushes), floss or flossers (e.g., dental floss), irrigators (e.g., oral irrigators), picks (e.g., dental picks or toothpicks), scrapers (e.g., tongue cleaners or scrapers), spatulas, sticks, retainers or mouth guards, etc.

The terms "treat", "treating," or "treatment," as used herein, refer to partially or completely alleviating, inhibiting, ameliorating, or relieving the disease or condition from which the subject is suffering. This means any manner in which one or more of the symptoms of a disease or disorder (e.g., plaque or periodontal disease) are ameliorated or otherwise beneficially altered. As used herein, amelioration of the symptoms of a particular disorder (e.g., plaque) refers to any lessening, whether permanent or temporary, lasting or transient that can be attributed to or associated with treatment by the compositions and methods of the present invention. In some embodiments, treatment can promote or result in, for example, a decrease in amount of plaque (e.g., in a subject) relative to the amount of plaque prior to treatment; or reductions in one or more symptoms associated with one or more periodontal diseases (e.g., gingivitis) in a subject relative to the subject's symptoms prior to treatment.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease in a subject. The prevention may also be partial, such that the occurrence of the disease in a subject is less than, occurs later than, or develops more slowly than that which would have occurred without the present invention.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. Moreover, treatment of a subject with a therapeutically effective amount of the compounds or compositions described herein can include a single treatment or a series of treatments. For example, effective amounts can be administered at least once. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health or age of the subject, and other diseases present.

Following administration, the subject can be evaluated to detect, assess, or determine their level of disease. In some instances, treatment can continue until a change (e.g., reduction) in the level of disease in the subject is detected. Upon improvement of a patient's condition (e.g., a change (e.g., decrease) in the level of disease in the subject), a maintenance dose of a compound, or composition disclosed herein can be administered, if necessary. Subsequently, the dosage or frequency of administration, or both, can be reduced, e.g., as a function of the symptoms, to a level at which the improved condition is retained. Patients may, however, require intermittent treatment on a long-term basis upon any recurrence of disease symptoms.

EXAMPLES

Example 1: Materials

Twenty-one amino acids that comprise the bulk of the amino acids found in humans were tested for their potential effects on intra-oral pH. These amino acids included: glycine, alanine, glutamic acid, glutamine, aspartic acid, valine, histidine, leucine, isoleucine, cystine, cysteine, arginine, lysine, phenylalanine, serine, tyrosine, threonine, proline, methionine, tryptophan, and asparagine. Samples of each amino acid were obtained (Sigma-Aldrich, St. Louis, Mo.) for study of their acidic and alkalinic tendencies within the human oral cavity, as it relates to elements of periodontitis pathology (e.g., dental caries, dental calculus, and gingivitis).

Example 2: Methods

To obtain human salivary sediment for performance of the experiments described herein, paraffin wax (4.02 g) was chewed by human subjects (including some subjects 70+ years of age, where oral alkalinity is commonly more prevalent) to stimulate the flow of saliva. Prior to the experiment, the subjects fasted for 12 hours and abstained from oral hygiene for at least 24 hours (to enable spontaneous dental plaque bacterial growth and buildup on their teeth and other oral surfaces (Kleinberg. I., 1967, Arch. Oral Biol., 1457-1473)). As a result of this process, oral bacteria were dislodged by the inert paraffin wax from the teeth and oral soft tissue surfaces in the mouths of the human subjects. About 40 ml of whole saliva was then collected from each subject by expectoration into a 50 ml polypropylene centrifuge tube chilled by surrounding it with cracked ice (Korayem, M. R., Traudt, M., and Kleinberg, I., 1990; Sandham, H. J. and Kleinberg, I., 1973).

The saliva collected was centrifuged at 1740 g in an International Equipment Company clinical centrifuge (Needham Heights, Mass.) for 15 min. at 4° C. The supernatant was decanted and discarded. To wash the remaining bacterial sediment, 40 ml of ice-cold distilled water was added and mixed in a vortex mixer. The resulting sediment-water mixture was centrifuged at 1740 g for 15 min. at 4° C. The supernatant was again decanted and discarded. This bacterial sediment washing procedure was repeated twice. To the washed bacterial sediment, 10 ml of deionized water was added and the composition was then mixed briefly and thoroughly in a vortex mixer. The sediment was transferred to a 15 ml polypropylene centrifuge tube. The resulting suspension was centrifuged at 1740 g for 15 min. at 4° C. and the resulting supernatant was aspirated and discarded.

To the packed 1.0 ml of salivary sediment obtained after centrifugation, 1.0 ml of deionized water was added to make a 50% salivary sediment suspension for the preparation of the following standard incubation mixtures: salivary sediment at 16.7% (v/v), with and without added individual amino acids: serine, glycine, alanine, valine, and/or histidine, etc. at either a 90 or 120 mM concentration; and leucine, isoleucine, aspartic acid, glutamine, cysteine, cystine, lysine, arginine, tyrosine, phenylalanine, threonine, proline, methionine, tyrosine, glutamine, and/or asparagine, each at 9 mM. These mixtures were each prepared in the presence or absence of 28 mM urea, which has a relatively high pH.

The initial pH of the incubation mixtures was carefully adjusted to or near 7.0 with either 1.0 M NaOH or 1.0 M HCl. Each bacterial mixture was then incubated overnight in a water bath at 37° C. The pH of each mixture was then determined using a combined pH and reference electrode (Radiometer Analytical SAS, Villeurbanne, France) at predetermined time intervals.

Separately, incubation mixtures containing salivary sediment at 16.7% (v/v) and 6.7 or 8.3 mM serine in the presence or absence of 6.7 mM urea, 20 or 25 mM serine and/or 3 mM sodium phytate (Sigma-Aldrich, St. Louis, Mo.), both in the presence or absence of 6.7 mM urea were prepared. Mixtures were incubated overnight at 37° C. in a water bath incubator (Kleinberg, I. and Hall, G., 1968; Salako, N. O. and Kleinberg, I., 1989), after adjusting the initial pH to or near 7.0 with 1N NaOH or 1N HCl.

Separately, incubation mixtures containing salivary sediment at 16.7% (v/v), 20 or 25 mM serine, and 6 mM sodium phytate were prepared in the presence or absence of 6.7 mM urea. Mixtures were incubated overnight at 37° C. in a water bath incubator, after adjusting the initial pH to or near 7.0 with 1N NaOH or 1N HCl.

Separately, incubation mixtures containing salivary sediment at 16.7% (v/v), 238 mM serine, and 6 mM sodium phytate were prepared in the presence or absence of 6.7 mM urea. Mixtures were incubated overnight at 37° C. in a water bath incubator, after adjusting the initial pH to or near 7.0 with 1N NaOH or 1N HCl.

Separately, incubation mixtures were prepared containing a sample of human molar tooth (e.g., enamel crown with undesirable exposed dentin covered by and hence painted over with inert nail polish (FIG. 23)), along with salivary sediment at 16.7% (v/v), 238 mM serine, and 6.0 mM sodium phytate, optionally with one or more other amino acids at the concentrations recited above, in the presence or absence of 6.7 mM urea. Aliquots (200 µl) from each incubation mixture were withdrawn at 0, 1, 2, 4, and 21 hours of incubation and centrifuged at 10,000 g for 10 min. at 4° C. Supernatants were stored at −20° C. for subsequent analysis of calcium by atomic absorption spectroscopy 3110 (PerkinElmer, Norwalk, Conn.).

Similar incubation mixtures were also prepared containing a sample of tooth cementum (e.g., from the roots of human molar teeth (FIG. 24)). The tooth coronal surfaces were partially covered with inert nail polish (Sally Hanson, Del Laboratory Inc., Garden City, N.Y.), and then prepared and incubated in similar fashion described above for the mixtures containing a sample of human molar tooth. Aliquots (200 µl) from each incubation mixture were withdrawn at 0, 1, 2, 4, and 21 hours of incubation and centrifuged at 10,000 g for 10 min. at 4° C. Supernatants were stored at −20° C. for subsequent analysis of calcium by atomic absorption spectroscopy 3110 (PerkinElmer, Norwalk, Conn.).

Separately, incubation mixtures containing salivary sediment at 16.7% (v/v), 238 mM serine, and 6 mM sodium phytate, with or without 6.7 mM urea, were prepared and incubated without adjusting the initial pH to or near 7.0, except for salivary sediment mixed with deionized water, which was adjusted to pH 8.10 with 1 M NaOH. Determination of the pH of each of these experimental entities were carried out at pre-determined time intervals (i.e., at 0 min., 15 min., 30 min., 1 h, 2 h, 3 h, 4 h, and 21 h) with a pH meter (Radiometer Copenhagen, type PHM26, Radiometer America, Westlake, Ohio) and a combination pH electrode (Radiometer Analytical, Cedex, France).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Biswas, S. D. and Kleinberg, I. 1971. Effect of urea concentration on its utilization, on the pH and the formation of ammonia and carbon dioxide in the human salivary sediment system. *Arch. Oral Biol.* 16: 759-780.
2. Denepitiya L. and Kleinberg I. 1982. A comparison of the microbial composition of pooled human dental plaque and salivary sediment. *Arch. Oral Biol.* 27: 739-745.
3. Golub, L. M., Borden, S. M., and Kleinberg, I. 1971. Urea content of gingival crevicular fluid and its relation to periodontal disease in humans. *J. Periodont. Res.* 6: 243-251.
4. Grases, F., Perelló, J., Sanchis, P., Isern, B., Prieto, R. M., Costa-Bauzá, A., Santiago, C., Ferragut, M. L., and Frontera, G. 2009. Anticalculus effect of a triclosan mouthwash containing phytate: a double-blind, randomized, three-period cross over trial. *J. Periodont. Res.* 44: 616-621.
5. Grenby, T. H. 1967. Phytates in decalcification tests in vitro. *Arch. Oral Biol.* 12: 531-537.
6. Heaney, R. P., Weaver, C. M., and Fitzsimmons, M. L. 1991. Soybean phytate content: effect on calcium absorption. *Am. J. Clin. Nutr.* 53: 745-747.
7. Kaufman, W. and Kleinberg, I. 1971. Effect of pH on calcium binding by phytic acid and its inositol phosphoric acid derivatives and on the solubility of their calcium salts. *Arch. Oral Biol.* 16: 445-460.
8. Kleinberg, I. 1967. Effect of urea concentration on human plaque pH levels in situ. *Arch. Oral. Biol.* 12: 1475-1484.
9. Kleinberg. I. 1967. Effect of varying sediment and glucose concentrations of the pH and acid production in human salivary sediment mixtures. *Arch. Oral. Biol.* 12: 1457-1473.
10. Kleinberg, I. and Hall, G. 1968. pH and depth of gingival crevices in different areas of the mouths of fasting humans. *J. Periodont. Res.* 3: 109-117.
11. Kleinberg, I., Craw, D., and Komiyma, K., 1973. Effect of salivary supernatant on the glycolytic activity of the bacteria in salivary sediment. *Arch. Oral Biol.* 18: 787-798.
12. Kleinberg, I., Kanapka, J. A., and Craw, D. 1977. The effect of saliva and salivary factors on the metabolism of the mixed oral flora, in *Microbial Aspects of Dental Caries*. Stiles, H. M., Loesche, W. J. and O'Brien, T. C., Eds. Information Retrieval Inc., Washington, D.C., 433.
13. Kleinberg, I., Kanapka, J. A., Chatterjee, R., Craw, D., D'Angelo, N., and Sandham, H. J. 1979. Metabolism of nitrogen by the oral mixed bacteria, in *Saliva and Dental Caries*. Kleinberg, I., Ellison, S. A., and Mandel, I. D., Eds. Information Retrieval, Inc., New York, N.Y., 357.
14. Korayem, M. R., Traudt, M., and Kleinberg, I. 1990. Oxygen uptake and its relation to pH in a human salivary system during fermentation of glucose. *Arch. Oral Biol.* 35: 759-764.
15. Jacobson, M. and Kesel, R. G. 1950. Salivary ammonia and its correlation to dental calculus. *J. Dent. Res.* 29: 364-374.
16. Takhashi, N. 2005. Microbial ecosystem in the oral cavity: Metabolic diversity in an ecological niche and its relationship with oral diseases. *Int. Congr. Ser.* 1284: 103-112.
17. Onosi, M., Tachibana, Y., Nakamura, T., Takakuwa, S., and Ishioka, K. 1957. Preferential sites of the urea hydrolyzing organisms in the mouth. *Tokyo Med. Dent. Bull.* 4, 253-257.
18. Salako, N. O. and Kleinberg, I. 1989. Incidence of selected ureolytic bacteria in human dental plaque from sites with differing salivary access. *Arch. Oral Biol.* 34: 787-791.

19. Sandham, H. J. and Kleinberg, I. 1973. Effect of fluoride on carbon dioxide and acid formation in salivary sediment mixtures incubated with glucose. *Arch. Oral Biol.* 18: 211-225.
20. Singer, D. L. and Kleinberg, I. 1978. Ammonia and urea content of human incisor plaques. *Arch Oral Biol.* 23: 1983-1987.
21. Jin, Y. and Yip, H.-K. 2002. Supragingival calculus: Formation and Control. *Crit. Rev. Oral Biol. Med.* 13: 426-441.

What is claimed is:

1. An oral composition for treating periodontitis and dental calculus accumulation, comprising:
    serine at a concentration of between about 6.7 and about 238 mM;
    at least one organic mono-phosphate or multi-phosphate salt at a concentration of between about 3 and about 6 mM;
    a buffer providing the composition with a pH of between about 6.1 and about 7.0; and
    an orally acceptable dosage form, wherein introduction of the composition to the oral environment of a subject suffering from periodontitis or dental calculus accumulation, reduces the alkalinity and thereby increases calcium concentration in the saliva by dissolving the calculus.

2. The oral composition of claim 1, wherein the orally acceptable dosage form is selected from the group consisting of toothpaste, gum, mouthwash and chewable tablets.

3. The oral composition of claim 1, wherein the orally acceptable dosage form is a dentrifice or toothpaste.

4. The oral composition of claim 1, wherein the pH of the composition is between about 6.1 and about 6.3.

5. The oral composition of claim 1, wherein the pH of the composition is between about 6.7 and about 7.0.

6. The oral composition of claim 1, wherein the organic mono-phosphate or multi-phosphate salt is an organic salt.

7. The oral composition of claim 6, wherein the salt is an inositol.

8. The oral composition of claim 7, wherein the inositol is a phytate.

9. The oral composition of claim 8, wherein the phytate is sodium phytate.

10. The oral composition of claim 1, wherein the orally acceptable dosage form is selected from the group consisting of capsule, tablet, emulsion, aqueous suspension, dispersion, paste, powder, gum, and solution.

11. The oral composition of claim 1, wherein the orally acceptable dosage form comprises one or more carriers, one or more lubricating agents, or one or more diluents.

12. The oral composition of claim 11, wherein the carrier is lactose or corn starch, the lubricating agent is magnesium stearate, and the diluent is lactose or dried corn starch.

13. The oral composition of claim 1, wherein the orally acceptable dosage form comprises one or more sweetening, flavoring, or coloring agents.

14. A method of treating plaque or periodontal disease, the method comprising administering an effective amount of the oral composition of claim 1 to a subject having, or at risk of having, plaque or periodontal disease.

15. The method of claim 14, wherein the subject is a human.

16. The method of claim 14, wherein the periodontal disease is gingivitis.

17. The method of claim 14, wherein the oral composition is applied to one or more teeth of the subject.

18. The method of claim 17, wherein the oral composition is applied to the exposed enamel, dentine, or cementum of one or more teeth of the subject.

19. The method of claim 14, wherein about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, or 3-10000 mg/kg of serine is administered per day.

20. The method of claim 14, wherein about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, or 3-10000 mg/kg of at least one organic mono-phosphate or multi-phosphate salt is administered per day.

21. The oral composition of claim 1, wherein the oral composition further comprises a device.

22. The oral composition of claim 21, wherein the device is selected from the group consisting of brush, floss, flosser, irrigator, mouth guard, pick, retainer, scraper, spatula, and stick.

23. An oral composition consisting of serine, at least one organic mono-phosphate or multi-phosphate salt and a buffer providing a pH of between about 6.0 and about 9.5, in an orally acceptable dosage form.

* * * * *

UNITED STATES PATENT AND TRADEMARK OFFICE
CERTIFICATE OF CORRECTION

PATENT NO. : 10,076,481 B2
APPLICATION NO. : 15/587265
DATED : September 18, 2018
INVENTOR(S) : Israel Kleinberg and Robi Chatterjee Page 1 of 1

It is certified that error appears in the above-identified patent and that said Letters Patent is hereby corrected as shown below:

In the Claims

In Claim 3, delete "dentrifice" and insert -- dentifrice --.

Signed and Sealed this
Thirteenth Day of November, 2018

Andrei Iancu
*Director of the United States Patent and Trademark Office*